United States Patent
Evans Raab et al.

(10) Patent No.: US 11,872,192 B2
(45) Date of Patent: *Jan. 16, 2024

(54) RET INHIBITOR FOR USE IN TREATING CANCER HAVING A RET ALTERATION

(71) Applicant: BLUEPRINT MEDICINES CORPORATION, Cambridge, MA (US)

(72) Inventors: Erica Evans Raab, Cambridge, MA (US); Beni B. Wolf, Cambridge, MA (US)

(73) Assignee: BLUEPRINT MEDICINES CORPORATION, Cambridge, MA (US)

(*) Notice: Subject to any disclaimer, the term of this patent is extended or adjusted under 35 U.S.C. 154(b) by 88 days.

This patent is subject to a terminal disclaimer.

(21) Appl. No.: 17/377,885

(22) Filed: Jul. 16, 2021

(65) Prior Publication Data

US 2022/0175773 A1 Jun. 9, 2022

Related U.S. Application Data

(63) Continuation of application No. 17/127,041, filed on Dec. 18, 2020, now Pat. No. 11,273,160, which is a continuation of application No. 17/061,743, filed on Oct. 2, 2020, which is a continuation of application No. PCT/US2019/025655, filed on Apr. 3, 2019.

(60) Provisional application No. 62/741,683, filed on Oct. 5, 2018, provisional application No. 62/657,605, filed on Apr. 13, 2018, provisional application No. 62/656,297, filed on Apr. 11, 2018, provisional application No. 62/652,284, filed on Apr. 3, 2018.

(51) Int. Cl.
*A61K 31/506* (2006.01)
*A61P 35/00* (2006.01)
*A61K 9/00* (2006.01)
*A61P 35/04* (2006.01)

(52) U.S. Cl.
CPC .......... *A61K 31/506* (2013.01); *A61K 9/0053* (2013.01); *A61P 35/00* (2018.01); *A61P 35/04* (2018.01)

(58) Field of Classification Search
CPC .................................................. A61K 31/506
See application file for complete search history.

(56) References Cited

U.S. PATENT DOCUMENTS

| | | | |
|---|---|---|---|
| 8,088,806 B2 | 1/2012 | Zhang et al. | |
| 8,802,697 B2 | 8/2014 | Bifulco, Jr. | |
| 9,126,951 B2 | 9/2015 | Bifulco, Jr. | |
| 9,187,475 B2 | 11/2015 | Kawamura et al. | |
| 9,200,002 B2 | 12/2015 | Hodous et al. | |
| 9,216,172 B2 | 12/2015 | Kohno et al. | |
| 9,297,011 B2 | 3/2016 | Downing et al. | |
| 9,334,263 B2 | 5/2016 | Hodous et al. | |
| 9,340,514 B2 | 5/2016 | Bifulco, Jr. | |
| 9,434,700 B2 | 9/2016 | Bifulco, Jr. | |
| 9,499,522 B2 | 11/2016 | DiPietro et al. | |
| 9,688,680 B2 | 6/2017 | Hodous | |
| 9,695,165 B2 | 7/2017 | Bifulco, Jr. | |
| 9,884,861 B2 | 2/2018 | Hodous et al. | |
| 9,944,651 B2 | 4/2018 | Hodous et al. | |
| 9,994,552 B2 | 6/2018 | DiPietro et al. | |
| 9,994,575 B2 | 6/2018 | Hodous et al. | |
| 10,000,490 B2 | 6/2018 | Bifulco, Jr. | |
| 10,000,496 B2 | 6/2018 | Hodous et al. | |
| 10,017,512 B2 | 7/2018 | Wenglowsky et al. | |
| 10,030,005 B2 | 7/2018 | Brubaker et al. | |
| 10,035,789 B2 | 7/2018 | Brubaker et al. | |
| 10,183,928 B2 | 1/2019 | Kim et al. | |
| 10,196,436 B2 | 2/2019 | Miduturu | |
| 10,202,365 B2 | 2/2019 | Brooijmans et al. | |
| 10,221,154 B2 | 3/2019 | Bifulco, Jr. et al. | |
| 10,227,329 B2 | 3/2019 | Brubaker et al. | |
| 10,584,114 B2 | 3/2020 | Brubaker et al. | |
| 10,774,070 B2 | 9/2020 | Brooijmans et al. | |
| 11,273,160 B2 * | 3/2022 | Evans Raab | A61K 31/506 |
| 11,279,688 B2 | 3/2022 | Brubaker et al. | |
| 2012/0316137 A1 | 12/2012 | Huang et al. | |
| 2013/0096136 A1 | 4/2013 | Hata et al. | |
| 2013/0115313 A1 | 5/2013 | Charrier et al. | |
| 2013/0116280 A1 | 5/2013 | Ju et al. | |
| 2014/0187559 A1 | 7/2014 | Miduturu | |
| 2014/0221404 A1 | 8/2014 | Kohno et al. | |
| 2014/0243357 A1 | 8/2014 | Dar et al. | |
| 2014/0272951 A1 | 9/2014 | Chakravarti et al. | |
| 2015/0057335 A1 | 2/2015 | Kohno et al. | |

(Continued)

FOREIGN PATENT DOCUMENTS

| | | | |
|---|---|---|---|
| CN | 104844567 A | 8/2015 | |
| CN | 105255927 A | 1/2016 | |

(Continued)

OTHER PUBLICATIONS

Mcmahon et al (2000).*

(Continued)

*Primary Examiner* — Paul V Ward
(74) *Attorney, Agent, or Firm* — Goodwin Procter LLP

(57) ABSTRACT

Disclosed herein are methods for treating a subject afflicted with a cancer having an activating RET alteration by administering an effective amount of a selective RET inhibitor, e.g., Compound 1 or pharmaceutically acceptable salts thereof, including, e.g., administering an amount of 60 mg to 400 mg of the selective RET inhibitor once daily.

19 Claims, 15 Drawing Sheets

(56) References Cited

U.S. PATENT DOCUMENTS

| | | |
|---|---|---|
| 2015/0177246 A1 | 6/2015 | Shibata et al. |
| 2016/0102097 A1 | 4/2016 | Hodous et al. |
| 2017/0014413 A1 | 1/2017 | Downing et al. |
| 2017/0022206 A1 | 1/2017 | Hodous et al. |
| 2017/0029409 A1 | 2/2017 | DiPietro et al. |
| 2017/0057953 A1 | 3/2017 | Hodous et al. |
| 2017/0066773 A1 | 3/2017 | Wenglowsky et al. |
| 2017/0066812 A1 | 3/2017 | Bifulco, Jr. |
| 2017/0121312 A1 | 5/2017 | Brubaker et al. |
| 2017/0145018 A1 | 5/2017 | Wenglowsky et al. |
| 2017/0174652 A1 | 6/2017 | Bifulco, Jr. |
| 2017/0204104 A1 | 7/2017 | Hodous et al. |
| 2017/0253593 A1 | 9/2017 | Bifulco, Jr. et al. |
| 2017/0267661 A1 | 9/2017 | Kim et al. |
| 2017/0281633 A1 | 10/2017 | Boylan et al. |
| 2017/0298069 A1 | 10/2017 | Brooijmans et al. |
| 2018/0022731 A1 | 1/2018 | Brooijmans et al. |
| 2018/0022732 A1 | 1/2018 | Brubaker et al. |
| 2018/0030032 A1 | 2/2018 | Brubaker et al. |
| 2019/0185454 A1 | 6/2019 | Brubaker et al. |
| 2019/0192522 A1 | 6/2019 | Hagel et al. |
| 2020/0407341 A1 | 12/2020 | Brubaker et al. |
| 2021/0085680 A1 | 3/2021 | Evans Raab et al. |
| 2021/0100795 A1 | 4/2021 | Evans Raab et al. |
| 2021/0100799 A1 | 4/2021 | Evans Raab et al. |
| 2021/0308134 A1 | 10/2021 | Hata et al. |
| 2022/0315560 A1 | 10/2022 | Brubaker et al. |
| 2023/0203009 A1 | 6/2023 | Waetzig et al. |

FOREIGN PATENT DOCUMENTS

| | | |
|---|---|---|
| CN | 107980784 A | 5/2018 |
| CN | 108341782 A | 7/2018 |
| CN | 111362923 A | 7/2020 |
| CN | 111440151 A | 7/2020 |
| EP | 3037547 A1 | 6/2016 |
| JP | 2015109806 A | 6/2015 |
| WO | WO-2001/60816 A1 | 8/2001 |
| WO | WO-2004/009087 A1 | 1/2004 |
| WO | WO-2005/062795 A2 | 7/2005 |
| WO | WO-2007/023382 A2 | 3/2007 |
| WO | WO-2007/087245 A2 | 8/2007 |
| WO | WO-2007/124221 A1 | 11/2007 |
| WO | WO-2007/136103 A1 | 11/2007 |
| WO | WO-2008/061201 A1 | 5/2008 |
| WO | WO-2009/003136 A1 | 12/2008 |
| WO | WO-2009/007748 A2 | 1/2009 |
| WO | WO-2009/014637 A2 | 1/2009 |
| WO | WO-2009/100536 A1 | 8/2009 |
| WO | WO-2010/006432 A1 | 1/2010 |
| WO | WO-2010/111056 A1 | 9/2010 |
| WO | WO-2010/144359 A1 | 12/2010 |
| WO | WO-2010/144394 A1 | 12/2010 |
| WO | WO-2011/060295 A1 | 5/2011 |
| WO | WO-2013/077921 A2 | 5/2013 |
| WO | WO-2013/133367 A1 | 9/2013 |
| WO | WO-2013/170159 A1 | 11/2013 |
| WO | WO-2014/039971 A1 | 3/2014 |
| WO | WO-2014/050781 A1 | 4/2014 |
| WO | WO-2014/072220 A1 | 5/2014 |
| WO | WO-2014/130810 A1 | 8/2014 |
| WO | WO-2014/141187 A1 | 9/2014 |
| WO | WO-2014/147640 A2 | 9/2014 |
| WO | WO-2015/006875 A1 | 1/2015 |
| WO | WO-2015/079251 A1 | 6/2015 |
| WO | WO-2016/037578 A1 | 3/2016 |
| WO | WO-2016/038552 A1 | 3/2016 |
| WO | WO-2016/075224 A1 | 5/2016 |
| WO | WO-2016/127074 A1 | 8/2016 |
| WO | WO-2017/011776 A1 | 1/2017 |
| WO | WO-2017/079117 A1 | 5/2017 |
| WO | WO-2017/079121 A2 | 5/2017 |
| WO | WO-2017/079140 A1 | 5/2017 |
| WO | WO-2017/100642 A1 | 6/2017 |
| WO | WO-2017/145050 A1 | 8/2017 |
| WO | WO-2017/161269 A1 | 9/2017 |
| WO | WO-2017/178844 A1 | 10/2017 |
| WO | WO-2017/178845 A1 | 10/2017 |
| WO | WO-2018/017983 A1 | 1/2018 |
| WO | WO-2018/022761 A1 | 2/2018 |
| WO | WO-2018/049233 A1 | 3/2018 |
| WO | WO-2018/060714 A1 | 4/2018 |
| WO | WO-2018/064852 A1 | 4/2018 |
| WO | WO-2018/071447 A1 | 4/2018 |
| WO | WO-2018/071454 A1 | 4/2018 |
| WO | WO-2018/102455 A1 | 6/2018 |
| WO | WO-2018/136661 A1 | 7/2018 |
| WO | WO-2018/136663 A1 | 7/2018 |
| WO | WO-2018/183712 A1 | 10/2018 |
| WO | WO-2018/189553 A1 | 10/2018 |
| WO | WO-2018/213329 A1 | 11/2018 |
| WO | WO-2018/237134 A1 | 12/2018 |
| WO | WO-2019/001556 A1 | 1/2019 |
| WO | WO-2019/008172 A1 | 1/2019 |
| WO | WO-2019/126121 A1 | 6/2019 |
| WO | WO-2019/143977 A1 | 7/2019 |
| WO | WO-2019/143991 A1 | 7/2019 |
| WO | WO-2019/143994 A1 | 7/2019 |
| WO | WO-2019/195471 A1 | 10/2019 |
| WO | WO-2020/033838 A2 | 2/2020 |
| WO | WO-2021/243186 A1 | 12/2021 |
| WO | WO-2021/243192 A1 | 12/2021 |
| WO | WO-2022/120136 A1 | 6/2022 |

OTHER PUBLICATIONS

Pinedo et al (2000).*

U.S. Appl. No. 17/061,743, filed Oct. 2, 2020.*

Caira (1998) "Crystalline Polymorphism of Organic Compounds," Topics in Current Chemistry 198:163-208.

Cascone, T et al., "Significant Systemic and CNS Activity of RET Inhibitor Vandetanib Combined with mTOR Inhibitor Everolimus in Patients with Advanced NSCLC with RET Fusion", J. of Clinical Oncology 34, No. 15, 2 pages.

Hilfiker et al. (2006) "Relevance of Solid-state Properties for Pharmaceutical Products," Polymorphism in the Pharmaceutical Industry, XP002528052, 19 pages.

International Search Report and Written Opinion dated Aug. 16, 2021, in International Patent Application No. PCT/US2021/034823, filed May 28, 2021, by Blueprint Medicines Corp. (14 pages).

International Search Report and Written Opinion dated May 11, 2021, in International Patent Application No. PCT/US2021/034811, filed May 28, 2021, by Blueprint Medicines Corp. (16 pages).

Sentürk et al. (2020) "Quantitative bioanalytical assay for the selective RET inhibitors selpercatinib and pralsetinib in mouse plasma and tissue homogenates using liquid chromatography-tandem mass spectrometry," Journal of Chromatography B 1147:122131 8 pages.

Thackaberry et al. (2012) "Non-clinical toxicological considerations for pharmaceutical salt selection," Expert Opin. Drug Metab. Toxicol. 8(11):1419-1433.

Brown et al. (1984) "Heterocyclic Amplifiers of Phleomycin. IV Pyrimidinylpurines, Phenylpyrimidines and Related Systems with Basic Side Chains," Aust. J. Chem., 37:2093-101.

Hughes (2021) "Review of Synthetic Routes and Crystalline Forms of the Oncology Drugs Capmatinib, Selpercatinib, and Pralsetinib," Org. Process Res. Dev. 25:2192-2204.

International Search Report and Written Opinion dated Feb. 24, 2022, in International Patent Application No. PCT/US2021/061754, filed Dec. 3, 2021, by Blueprint Medicines Corp. (16 pages).

NCT03037385, entitled Phase 1/2 Study of the Highly-selective RET Inhibitor, Pralsetinib (BLU-667), in Patients With Thyroid Cancer, Non-Small Cell Lung Cancer, and Other Advanced Solid Tumors (ARROW) (13 pages).

NCT04222972, entitled AcceleRET Lung Study of Pralsetinib for 1L RET Fusion-positive, Metastatic NSCLC (11 pages).

Abdel-Rahman, O. and M. Fouad (2014) "Risk of cardiovascular toxicities in patients with solid tumors treated with sunitinib, axitinib, cediranib or regorafenib: an updated systematic review and comparative meta-analysis" Crit Rev Oncol Hematol,92:194-207.

(56) References Cited

OTHER PUBLICATIONS

Ahn M. et al. "OA 09.03 TATTON Ph lb Expansion Cohort: Osimertinib plus Savolitinib for Pts with EGFR-Mutant MET-Amplified NSCLC after Progression on Prior EGFR-TKI." J Thorac Oncol. 12(11) S1768, 2017.
Anonymous "BLU-667 Targets RET-Altered Cancers" Cancer Discovery, vol. 8, No. 6, OF8, Jun. 2018 (Jun. 2018), p. 5pp, XP002792436, Retrieved from the Internet: URL:http://cancerdiscovery.aacrjournals.or g/content/8/6/OF8.long [retrieved on Jun. 25, 2019].
Anonymous, "Phase 1 Study of the Highly-selective RET Inhibitor BLU-667 in Patients With Thyroid Cancer, Non-Small Cell Lung Cancer, and Other Advanced Solid Tumors," ClinicalTrials.org Internet Citation, Apr. 21, 2017 (Apr. 21, 2017), p. 8pp, XP002783685.
Anonymous: "Phase 1 Study of the Highly-selective RET Inhibitor BLU-667 in Patients With Thyroid Cancer, Non-Small Cell Lung Cancer, and Other Advanced Solid Tumors," Internet Citation, Apr. 21, 2017, Retrieved from the Internet: URL:https://www.clinicaltrials.gov/ct2/history/NCT03037385?V_3=View#StudyPageTop.
Antonescu, C.R. et al. (Jul. 2015) "Molecular Characterization of Inflammatory Myofibroblastic Tumors with Frequent ALK and ROS1 Fusions and Rare Novel RET Gene Rearrangement" Am J Surg Pathol, 39(7):957-967. HHS Public Access Author Manuscript;available in PMC Jul. 1, 2015 (19 pages).
Arighi, E. et al. (2005) "RET tyrosine kinase signaling in development and cancer" Cytokine & Growth Factor Reviews, 16:441-467.
Baselga, J. et al. (2005) "Phase II and Tumor Pharmacodynamic Study of Gefitinib in Patients with Advanced Breast Cancer" J Clin Oncol, 23(23):5323-5333.
Bentzien, F. et al. (2013) "In Vitro and in Vivo Activity of Cabozantinib (XL184), an Inhibitor of RET, MET, and VEGFR2, in a Model of Medullary Thyroid Cancer" Thyroid, 23(12):1569-1577.
Brandt, W. et al. (2010) "Inhibitors of the RET tyrosine kinase based on a 2-(alkylsulfanyl)-4-(3-thienyl) nicotinonitrile scaffold" Eur J Med Chem, 45:2919-2927.
Caprelsa (vandetanib) "Full Prescribing Information" Reference ID: 3964956, Cambridge, MA: Sanofi Genzyme; 2016.
Carlomagno, F. et al. (Feb. 1995) "Point Mutation of the Ret Proto-oncogene in the TT Human Medullary Thyroid Carcinoma Cell Line" Biochem Biophys Res Common, 207(3):1022-1028.
Ceccherini, I. et al. (1997) "Somatic in frame deletions not involving juxtamembranous cysteine residues strongly activate the RET proto-oncogene" Oncogene, 14:2609-2612.
Chalice Software Technical Guide, Horizon CombinatoRx Inc., Cambridge, MA, USA (downloaded Jul. 2018).
Chen, M-H et al. (2014) "Antitumor activity of the combination of a HSP90 inhibitor and a PI3K/mTOR dual inhibitor against cholangiocarcinoma," Oncotarget, 5(8):2372-2389.
Cometriq (cabozantinib)"Full Prescribing Information" Reference ID: 3964956, South San Francisco, CA: Exelixix, Inc.; 2018.
Druker, B.J. et al. (2001) "Efficacy and Safety of a Specific Inhibitor of the BCR-ABL Tyrosine Kinase in Chronic Myeloid Leukemia" New Engl J Med, 344(14):1031-1037.
Eisenhauer, E.A. et al. (2009) "New response evaluation criteria in solid tumours: Revised RECIST guideline (version 1.1)" Eur J Cancer, 45:228-247.
Elisei, R. et al. (2008) "Prognostic Significance of Somatic RET Oncogene Mutations in Sporadic Medullary Thyroid Cancer: A 10-Year Follow-Up Study" J Clin Endocrinol Metab, 93(3):682-687.
Engelman J.A. et al. "MET Amplification Leads to Gefitinib Resistance in Lung Cancer by Activating ERBB3 Signaling." Science, 2007, 316 (5827), pp. 1039-1043.
Evans, E. (May 1, 2016) "The Development of Potent and Selective RET Inhibitors" Slides presented at the 2016 Annual Meeting of the International Thyroid Oncology Group at the University of Colorado (19 pages).
Fagin, J.A. et al. "Biologic and Clinical Perspectives on Thyroid Cancer." N Engl J Med. 2016, 375 (11) pp. 1054-1067.

Fang, P. et al. (Feb. 2016) "Detection of a novel RET gene fusion in a non-small cell lung cancer patient using AMP chemistry" J Thorac Oncol, 11.2:S21-S22.
Gainor J.F. et al. "Dramatic Response to Combination Erlotinib and Crizotinib in a Patient with Advanced, EGFR-Mutant Lung Cancer Harboring De Novo MET Amplification." J Thorac Oncol. 11(7) 2016, pp. e83-e85.
Gautschi, O. et al. (2016) "Targeting RET in patients with RET-rearranged lung cancers: Results from a global registry" J Clin Oncol, 34(15S) (suppl; abstr 9014).
Gild, M.L. et al. (Oct. 2013) "Targeting mTOR in RET mutant medullary and differentiated thyroid cancer cells" Endocr Re/at Cancer, 20(5):659-667. HHS Public Access Author Manuscript; available in PMC Mar. 27, 2015 (16 pages).
Graham et al., 17 Bioorganic & Medicinal Chemistry, 5886-5893 (2007).
Grubbs, E.G. et al. (Mar. 2015) "RET Fusion as a Novel Driver of Medullary Thyroid Carcinoma" J Clin Endocrinol Metab, 100:788-793.
Halkova, T. et al. (2015) "A novel RET/PTC variant detected in a pediatric patient with papillary thyroid cancer without ionization history" Hum Pathol, 46:1962-1969.
Hayashi, H. et al. (2000) "Characterization of intracellular signals via tyrosine 1062 in RET activated by glial cell line-derived neurotrophic factor" Oncogene, 19:4469-4475.
Horiike, A. et al. (2016) "Sorafenib treatment for patients with RET fusion-positive non-small cell lung cancer" Lung Cancer, 93:43-46.
International Search Report and Written Opinion dated Apr. 29, 2016, in International Patent Application No. PCT/US2016/016808, filed Feb. 5, 2016, by Blueprint Medicines Corp. (8 pages).
International Search Report and Written Opinion dated Jan. 18, 2017, in International Patent Application No. PCT/US2016/059879, filed Nov. 1, 2016, by Blueprint Medicines Corp. (12 pages).
International Search Report and Written Opinion dated Jun. 12, 2017, in International Patent Application No. PCT/US2017/022969, filed Mar. 17, 2017, by Blueprint Medicines Corp. (12 pages).
International Search Report and Written Opinion dated Oct. 12, 2017, in International Patent Application No. PCT/US2017/043964, filed Jul. 26, 2017, by Blueprint Medicines Corp. (13 pages).
International Search Report and Written Opinion dated Oct. 25, 2017, in International Patent Application No. PCT/US2017/043340, filed Jul. 21, 2017, by Blueprint Medicines Corp. (14 pages).
International Search Report and Written Opinion dated Aug. 21, 2018, in International Patent Application No. PCT/US2018/032794, filed May 15, 2018, by Blueprint Medicines Corp. (18 pages).
International Search Report and Written Opinion of the International Searching Authority for Intenational Application No. PCT/US2019/025655 dated Jul. 23, 2019 (16 pages).
International Search Report and Written Opinion of the International Searching Authority for International Application No. PCT/US2019/045919 dated Jan. 22, 2020 (11 pages).
Jin, N. et al. (Oct. 1, 20115), "Synergistic Action of a RAF Inhibitor and a Dual PI3K/mTOR Inhibitor in Thyroid Cancer," Clin Cancer Res, 17(20):6482-6489.
Joung, J.Y. et al. (2016) "Diffuse sclerosing variant of papillary thyroid carcinoma: major genetic alterations and prognostic implications" Histopathology, 69:45-53.
Jovanovic, R. et al. (2015) "Novel RET Mutations in Macedonian Patients with Medullary Thyroid Carcinoma: Genotype-Phenotype Correlations" Prilozi, 36(1):93-107.
Karrasch, T. et al. (2016) "How to Assess the Clinical Relevance of Novel RET Missense Variants in the Absence of Functional Studies?" Eur Thyroid J, 5:73-77.
Kato, S. et al. (Apr. 15, 2017) "RET Aberrations in Diverse Cancers: Next-Generation Sequencing of 4,871 Patients" Clin Cancer Res, 23(8):1988-1997.
Kim, S.H. et al. (2015) "A New Germline ALA641 THR Variant in the Transmembrane Domain of the RET Gene Associated with Medullary Thyroid Cancer" Acta Endocrinologica (Buc), 11.2:189-194.
Klempner et al. "Emergence of RET rearrangement co-existing with activated EGFR mutation in EGFR-mutated NSCLC patients who

(56) References Cited

OTHER PUBLICATIONS had progressed on first- or second-generation EGFR TKI" Lung Cancer, Sep. 2015, vol. 89, No. 3, pp. 357-359; abstract, p. 358, col. 1, para 2, p. 359, col. 1, para 2.
Krampitz, G.W. and J.A. Norton (2014) "RET Gene Mutations (Genotype and Phenotype) of Multiple Endocrine Neoplasia Type 2 and Familial Medullary Thyroid Carcinoma" Cancer, 120:1920-1931.
Kuster, B. (Ed.) (2012) *Kinase Inhibitors. Methods and Protocols*. Humana Press; Chapters 1 and 2, pp. 1-44.
Latteyer, S. et al. (Mar. 2016) "A 6-Base Pair in Frame Germline Deletion in Exon 7 of RET Leads to Increased RET Phosphorylation, ERK Activation, and MEN2A" J Clin Endocrinol Metab, 101(3):1016-1022.
Le Rolle, A. et al. (2015) "Identification and characterization of RET fusions in advanced colorectal cancer" Oncotarget, 6(30):28929-28937.
Lee, M.S. et al. (2016) "Efficacy of the combination of MEK and CDK4/6 inhibitors in vitro and in vivo in KRAS mutant colorectal cancer models" Oncotarget, 7(26):39595-39608.
Lehar, J. et al. (2009) "Synergistic drug combinations improve therapeutic selectivity" Nat Biotechnol, 27(7):659-666. HHS Public Access Author Manuscript; available in PMC Jan. 1, 2010 (23 pages).
Lin, J.J. et al. (2016) "Clinical Activity of Alectinib in Advanced RET-Rearranged Non-Small Cell Lung Cancer" J Thorac Oncol, 11(11):2027-2032.
Lipson, D. et al. (2012) "Identification of new ALK and RET gene fusions from colorectal and lung cancer biopsies" Nat Med, 18(3):382-384. HHS Public Access Author Manuscript; available in PMC Feb. 6, 2014 (7 pages).
Machens, A et al. (2003) "Early Malignant Progression of Hereditary Medullary Thyroid Cancer" New Engl J Med, 349:1517-1525.
Mologni, L. et al. (2010) "Synthesis, structure-activity relationship and crystallographic studies of 3-substituted indolin-2-one RET inhibitors" Bioorg Med Chem, 18:1482-1496.
Mologni, L. et al. (2013) "Ponatinib is a potent inhibitor of wild-type and drug-resistant gatekeeper mutant RET kinase" Mol Cell Endocrinol, 377:1-6.
Mologni, L. et al. (2017) "RET kinase inhibitors: a review of recent patents (2012-2015)" Exp Opin Ther Patents, 27(1):91-99.
Moura, M.M. et al. (2009) "Correlation of RET somatic mutations with clinicopathological features in sporadic medullary thyroid carcinomas" Br J Cancer, 100:1777-1783.
Mulligan, L.M. (Mar. 2014) "RET revisited: expanding the oncogenic portfolio" Nat Rev Cancer, 14:173-186.
Mulligan, L.M. et al. (1995) "Genotype-phenotype correlation in multiple endocrine neoplasia type 2: report of the International RET Mutation Consortium" J Int Med, 238:343-346.
Mulligan, L.M. et al. (Jun. 3, 1993) "Germ-line mutations of the RET proto-oncogene in multiple endocrine neoplasia type 2A" Nature, 363:458-460.
Oxnard, G.R. et al. "Assessment of Resistance Mechanisms and Clinical Implications in Patients With EGFR T790M-Positive Lung Cancer and Acquired Resistance to Osimertinib." JAMA Oncol. 2018, 4(11), pp. 1527-1534.
Pirker, R. and M. Filipits (2015) "Alectinib in RET-rearranged non-small cell lung cancer—Another progress in precision medicine?" Transl Lung Cancer Res, 4(6):797-800.
Plaza-Menacho, I. et al. (2014) "Mechanisms of RET signaling in cancer: Current and future implications for targeted therapy" Cellular Signalling, 26:1743-1752.
Qi, X. et al. (2015) "RET mutation p.S891A in a Chinese family with familial medullary thyroid carcinoma and associated cutaneous amyloidosis binding OSMR variant p.G513D" Oncotarget, 6(32):33993-34003.
Rahal, R. (Apr. 18, 2016) "The development of potent, selective RET inhibitors" Slides of a Presentation at the American Association for Cancer Research (AACR) Annual Meeting, Apr. 16-20, 2016, New Orleans (15 pages).
Rahal, R. et al. "BLU-667 is a Potent and Highly Selective RET Inhibitor Being Developed for RET—Driven Cancers," Poster B151, Blueprint Medicines Corporation (1 page).
Rahal, R. et al. (2016) "The development of potent, selective RET inhibitors that target both wild-type RET and prospectively identified resistance mutations to multi-kinase inhibitors" Abstract submitted to the American Association for CancerResearch (AACR) Annual Meeting, Apr. 16-20, 2016, New Orleans; submission date Dec. 1, 2015 (2 pages).
Ramalingam et al. "Osimertinib As First-Line Treatment of EGFR Mutation-Positive Advanced Non-Small-Cell Lung Cancer" Journal Of Clinical Oncology, Mar. 20, 2018, vol. 36, No. 9, p. 841-849; abstract.
Reagan-Shaw et al. (2007) "Dose translation from animal to human studies revisited" The FASEB Journal, 22:659-661.
Reckamp, K. L. et al. "Abstract 936: Analysis of cell-free DNA from 32,991 advanced cancers reveals novel co-occurring activating RET alterations and oncogenic signaling pathway aberrations." Cancer Research. Pubished Jul. 2018. Proceedings: AACR Annual Meeting 2018; Apr. 14-18, 2018; Chicago, IL. Retrieved from the internet URL: "<https://cancerres.aacrjournals.org/content/78/13_Supplement/936>" (3 pages).
Robinett, R.G. et al. (2007) "The discovery of substituted 4-(3-hyroxyanilino)-quinolines as potent RET kinase inhibitors" Bioorg Med Chem Lett, 17:5886-5893.
Robinson B. G. et al. "Vandetanib (100 mg) in Patients with Locally Advanced or Metastatic Hereditary Medullary Thyroid Cancer," Journal of Clinical En Doc Ri No Logy and Metabolism, vol. 95, No. 6, Jun. 1, 2010 (Jun. 1, 2010), pp. 2664-2671, XP055599340.
Romei, C. et al. (Apr. 2016) "A comprehensive overview of the role of the RET proto-oncogene in thyroid carcinoma" Nat Rev Endocrinol, 12:192-202.
Saito, M. et al. (Jun. 2016) "Gene aberrations for precision medicine against lung adenocarcinoma" Cancer Sci, 107(6):713-720.
Sarker, D. and P. Workman (2007) "Pharmacodynamic Biomarkers for Molecular Cancer Therapeutics" Adv Cancer Res, 96:213-268.
Schrock, A.B. et al. "Receptor Tyrosine Kinase Fusions and BRAF Kinase Fusions are Rare but Actionable Resistance Mechanisms to EGFR Tyrosine Kinase Inhibitors." Translational Oncology, 2018, 13 (9) pp. 1312-1323.
Scollo, C. et al. (2016) "A novel RET gene mutation in a patient with apparently sporadic pheochromocytoma" Endocr J, 63(1):87-91.
Silva, A.L. et al. (2015) "Identification and characterization of two novel germline RET variants associated with medullary thyroid carcinoma" Endocrine, 49:366-372.
Stransky, N. et al. (2014) "The landscape of kinase fusions in cancer" Nat Commun, 5:4846 (10 pages).
Subbiah et al. Abstract CT043 "Highly potent and selective RET inhibitor, BLU-667, achieves proof of concept in a phase I study of advanced, RET-altered solid tumors," Cancer Research vol. 78, No. 13, Supplement Jul. 1, 2018 (Jul. 2018), XP002792435, Proceedings: AACR Annual Meeting 2018; Apr. 14-18, 2018; Chicago, IL. Retrieved from the Internet: URL:http://cancerres.aacrjournals.org/cont ent/78/13 Supplement/CT043 [retrieved on Jun. 26, 2019].
Subbiah V. et al. "Precision Targeted Therapy with BLU-667 for RET-Driven Cancers," Cancer Discovery, vol. 8, No. 7, Apr. 15, 2018 (pp. 836-849).
Subbiah, V. et al. (Jul. 2015) "Systemic and CNS activity of the RET inhibitor vandetanib combined with the mTOR inhibitor everolimus in KIF5B-RET re-arranged Non-Small Cell Lung Cancer with brain metastases" Lung Cancer, 89(1):76-79. HHS Public Access Author Manuscript; available in PMC Aug. 25, 2016 (10 pages).
Suehara, Y. et al. (Dec. 15, 2012) "Identification of KIF5B-RET and GOPC-ROS1 fusions in lung adenocarcinomas through a comprehensive mRNA-based screen for tyrosine kinase fusions" Clin Cancer Res, 18(24):6599-6608. HHS Public Access AuthorManuscript; available in PMC Nov. 17, 2014 (18 pages).
Suzuki, M. et al. (Jul. 2013) "Identification of a lung adenocarcinoma cell line with CCDC6-RET fusion gene and the effect of RET inhibitors in vitro and in vivo" Cancer Sci, 104(7):896-903.
Takeuchi, K. et al. (Mar. 2012) "RET, ROS1 and ALK fusions in lung cancer" Nat Med, 18(3):378-381.

(56) References Cited

OTHER PUBLICATIONS

Tan, D.S. et al. (2009) "Biomarker-Driven Early Clinical Trials in Oncology" Cancer J, 15(5):406-420.

Touat, M. et al. (2015) "Targeting FGFR Signaling in Cancer" Clin Cancer Res, 21(12):2684-2694.

U.S. Nat'l Library of Med., A Phase 1 Trial of Vandetanib (a Multi-kinase Inhibitor of EGFR, VEGFR and RET Inhibitor) in Combination With Everolimus (an mTOR Inhibitor) in Advanced Cancer, ClinicalTrials.gov,https://clinicaltrials.gov/ct2/show/NCT01582191 (last updated Jul. 3, 2018) (7 pages).

U.S. Nat'l Library of Med., Phase 1 Study of the Highly-selective RET Inhibitor BLU-667 in Patients With Thyroid Cancer, Non-Small Cell Lung Cancer, and Other Advanced Solid Tumors, ClinicalTrials.gov, https://clinicaltrials.gov/ct2/show/NCT03037385(last updated Jun. 27, 2018) (8 pages).

Wang, L. et al. (2012) "Identification of a Novel, Recurrent HEY1-NCOA2 Fusion in Mesenchymal Chondrosarcoma based on a Genome-wide Screen of Exon-level Expression Data" Genes Chromosomes Cancer, 51(2):127-139. HHS Public Access Author Manuscript;available in PMC Feb. 1, 2013 (24 pages).

Wang, R. et al. (Dec. 10, 2012) "RET Fusions Define a Unique Molecular and Clinicopathologic Subtype of Non-Small-Cell Lung Cancer" J Clin Oncol, 30(35):4352-4359.

Wells, S.A. et al. (2015) "Revised American Thyroid Association Guidelines for the Management of Medullary Thyroid Carcinoma" Thyroid, 25(6):567-610.

Anonymous "Estimating the Maximum Safe Starting Dose in Initial Clinical Trials for Therapeutics in Adult Healthy Volunteers", Guidance for Industry, Jul. 1, 2005 (Jul. 1, 2005), pp. 1-30, XP093000005, Retrieved from the Internet: URL:https://www.fda.gov/media/ 72309/download [retrieved on Nov. 21, 2022].

Chilean Search Report dated Jun. 27, 2022, in Chilean Patent Application No. 202002544, Chilean National Stage of International Patent Application No. PCT/US2019/025655, filed Apr. 3, 2019, by Blueprint Medicines Corp.

Chilean Search Report dated Mar. 16, 2023, in Chilean Patent Application No. 202002544, Chilean National Stage of International Patent Application No. PCT/US2019/025655, filed Apr. 3, 2019, by Blueprint Medicines Corp.

Drilon et al. (2018) "Targeting RET-driven cancers: lessons from evolving preclinical and clinical landscapes," *Nature Reviews Clinical Oncology* 15:151-167.

Ferrara et al. "Clinical and Translational Implications of RET Rearrangements in Non-Small Cell Lung Cancer," Journal of Thoracic Oncology, 2018, 13, pp. 27-45.

Kamil et al. "Dose estimation, conversion and translation from animal to human and human to animal for clinical and animal studies", Int. J. Biol. Biotech., Jul. 1, 2017 (Jul. 1, 2017), pp. 311-317, XP093000013, Retrieved from the Internet: URL:https://www.researchgate.net/publication/322329638_Dose_estimation_conversion_and_translation_from_animal_to_human_and_human_to_animal_for_clinical_and_animal_studies [retrieved on Nov. 21, 2022].

Kohno et al. (2023) "RET fusion gene: Translation to personalized lung cancer therapy," Cancer Sci 104(11):1396-1400.

NCT03037385, entitled "Phase 1 Study of BLU-667 in Patients With Thyroid Cancer, Non-Small Cell Lung Cancer, and Other Advanced Solid Tumors," ClinicalTrials.gov, Jan. 17, 2018 (8 pages).

NCT03037385, entitled "Phase 1 Study of BLU-667 in Patients With Thyroid Cancer, Non-Small Cell Lung Cancer, and Other Advanced Solid Tumors," ClinicalTrials.gov, Jan. 27, 2017 (7 pages).

Piotrowska et al.(2018) "MA26.03 Activity of Osimertinib and the Selective RET Inhibitor BLU-667 in an EGFR-Mutant Patient with Acquired RET Rearrangement," Journal of Thoracic Oncology—IASLC 19th World Conference on Lung Cancer, Sep. 23, 2018, pp. S451-S451.

Piotrowska et al. (2018) "Landscape of Acquired Resistance to Osimertinib in EGFR-Mutant NSCLC and Clinical Validation of Combined EGFR and RET Inhibition with Osimertinib and BLU-677 for Acquired RET Fusion," Cancer Discovery 8(12):1529-1539.

Pound et al. "Is it possible to overcome issues of external validity in preclinical animal research? Why most animal models are bound to fail", J. Transl Med, Jan. 1, 2018 (Jan. 1, 2018), pp. 1-8, XP093000231, DOI: 10.1186/s12967-018-1678-1 Retrieved from the Internet: URL:https://www.researchgate.net/publication/328793141_1s_it_possible_to_overcome_issues_of_external_validity_in_preclinical_animal_research_Why_most_animal_models_are_bound_to_fail [retrieved on Nov. 21, 2022].

Reckamp et al. (2014) "Phase II trial of XL184 (cabozantinib) plus erlotinib in patients (pts) with advanced EGFR-mutant non-small cell lung cancer (NSCLC) with progressive disease (PD) on epidermal growth factor receptor (EGFR) tyrosine kinase inhibitor (TKI) therapy: A California Cancer Consortium phase II trial (NCI 9303)," *Journal of Clinical Oncology* 32(15)8014 4 pages.

Russian Search Report dated Jan. 13, 2023, in Russian Patent Application No. 2020135917, Russian National Stage of International Patent Application No. PCT/US2019/025655, filed Apr. 3, 2019, by Blueprint Medicines Corp.

Singapore Written Opinion dated Dec. 13, 2021, in Singapore Patent Application No. 11202009681Y, Singapore National Stage of International Patent Application No. PCT/US2019/025655, filed Apr. 3, 2019, by Blueprint Medicines Corp.

Subbiah et al. "Clinical activity and safety of the RET inhibitor pralsetinib in patients with RET fusion-positive solid tumours: update from the ARROW trial", ASCO, Jun. 4, 2021 (Jun. 4, 2021), pp. 1-1, XP093000210, Retrieved from the Internet: URL:https://ascopubs.org/doi/abs/10.1200/JCO.2021 .39.15_suppl.3079 [retrieved on Nov. 21, 2022].

Wakelee et al. (2017) "A phase Ib/II study of cabozantinib (XL184) with or without erlotinib in patients with non-small cell lung cancer," Cancer Chemother Pharmacol 79:923-932.

\* cited by examiner

RET INHIBITOR FOR USE IN TREATING CANCER HAVING A RET ALTERATION

This application is a continuation of U.S. patent application Ser. No. 17/127,041, filed Dec. 18, 2020 which application is a continuation of U.S. patent application Ser. No. 17/061,743, filed Oct. 2, 2020, which is a continuation of PCT/US2019/025655, filed Apr. 3, 2019, which claims priority to U.S. Provisional Application No. 62/652,284, filed Apr. 3, 2018, U.S. Provisional Application No. 62/656,297, filed Apr. 11, 2018, U.S. Provisional Application No. 62/657,605, filed Apr. 13, 2018, and U.S. Provisional Application No. 62/741,683, filed Oct. 5, 2018, the contents of each of which are incorporated by reference herein in their entirety.

This disclosure relates to methods for treating a subject afflicted with a cancer having an activating RET alteration by administering an effective amount of a selective RET inhibitor, i.e., a compound which is specifically designed to selectively target one or more RET or RET-altered kinases. As used herein, the term "afflicted with a cancer" means having a cancer. Said another way, a subject afflicted with a cancer has a cancer. More specifically, the methods described herein relate to treating a subject having a cancer characterized by an activating RET alteration. In some embodiments, the selective RET inhibitor is Compound 1 or pharmaceutically acceptable salts thereof. In some embodiments, the selective RET inhibitor is administered once daily. In some embodiments, the effective amount is 60 mg to 400 mg, 100 mg to 400 mg, 300 mg, or 400 mg. In some embodiments, the effective amount is 60 mg to 400 mg, 100 mg to 400 mg, 300 mg, or 400 mg administered once daily. In some embodiments, the cancer is a RET-altered solid tumor, a RET-altered non-small cell lung cancer, or a RET-altered thyroid cancer. In some embodiments, the cancer is a brain cancer, wherein the brain cancer is associated with non-small cell lung cancer. This disclosure also relates to methods of treating RET-altered cancers by administering a physiological effective dose of a selective RET inhibitor that produces a sustained down-regulation of at least one effect marker.

The receptor tyrosine kinase (RTK) RET, along with glial cell line-derived neurotrophic factors (GDNF) and GDNF family receptors-α (GFRα), is required for the development, maturation, and maintenance of several neural, neuroendocrine, and genitourinary tissue types. However, increasing evidence implicates aberrant activation of RET as a critical driver of tumor growth and proliferation across a broad number of solid tumors (Mulligan L M., *Nat. Rev. Cancer.* 14:173-186 (2014)). Oncogenic RET activation occurs via gain of function mutation or RET gene rearrangement resulting in the production of a RET fusion protein with constitutively active RET signaling that promotes ligand-independent tumor growth. Oncogenic RET activation was initially described in hereditary and sporadic thyroid cancers and subsequently in non-small cell lung cancer (NSCLC).

Oncogenic RET rearrangements have been identified in 1-2% of NSCLC (Lipson, D. et al., *Nat. Med.* 18:382-384 (2012); Takeuchi, K. et al., *Nat. Med.* 18:378-381 (2012); Stransky, N. et al., *Nat. Commun.* 5:4846 (2014)). This generates a constitutively active kinase that promotes tumorigenesis. As with anaplastic lymphoma kinase (ALK) and c-ros oncogene (ROS) 1-rearranged NSCLC, RET-rearranged NSCLC typically has adenocarcinoma histology (though occasionally squamous) and occurs in young, non-smoking patients. Because diagnostic testing for RET is not standard of care, RET-rearranged patients with advanced NSCLC are treated per NCCN guidelines for epidermal growth factor receptor (EGFR—) and ALK-negative adenocarcinoma. This usually includes chemotherapy with a platinum doublet or more recently with a checkpoint inhibitor however, clinical response and overall survival specifically in RET-rearranged NSCLC with these agents is not well understood. Subsequent therapy beyond chemotherapy and checkpoint inhibitors for refractory patients per NCCN guidelines is best supportive care or clinical trial.

Initial case reports and single-arm studies with the multikinase RET inhibitors (MKIs) cabozantinib, vandetanib, sorafenib, and alectinib in patients with known RET-rearranged NSCLC have demonstrated clinical activity, suggesting that RET may be a valid target in NSCLC. Although encouraging response rates (~12%-60%) (Horiike A et al., *Lung Cancer* 93:43-6 (Mar. 2016); Lin J J et al., *J Thorac Oncol.* 11(11):2027-32 (Nov. 2016); Gautshi O et al., *J Clin Oncol.* 34 (suppl; abstr 9014) (2016)) have been observed in these early studies, duration of response is typically less than a year. MKI treatment was associated with significant toxicity, requiring dose interruption and/or dose modification, which likely limit exposures required to effectively inhibit RET.

Oncogenic RET activation is also associated with thyroid cancer. Thyroid cancer consists primarily of differentiated thyroid cancer (DTC; ~90% of cases), medullary thyroid cancer (MTC; ~5% of cases), and anaplastic thyroid cancer (<5% of cases). DTC arises sporadically from thyroid follicular cells and consists of papillary thyroid cancer (PTC) (~80% of all thyroid cancer cases) and follicular thyroid cancer. In contrast, MTC arises from parafollicular C cells and occurs in both hereditary and sporadic forms. Oncogenic RET activation has been implicated as a driver in both MTC and PTC.

Recurrent gene rearrangements involving RET and a dimerization domain-encoding gene have been identified in approximately 5%-20% of sporadic papillary tumors in adults. Kinase-activating RET mutations occur in nearly all cases of hereditary MTC (87%-97%) (Machens A et al., *N Engl J Med* 349:1517-25 (2003); Mulligan L M et al., *Nature* 363(6428):458-60 (1993 Jun. 3); Mulligan L M et al., *J Int Med.* 238(4):343-346 (1995)) and approximately 43%-65% of sporadic MTC (Elisei R. et al., *J Clin Endocrinol Metab.* 93:682-687 (2008); Moura M M et al., *British Journal of Cancer* 100:1777-1783 (2009)). These RET mutations occur in the extracellular domain (primarily at the C634 position) which promote ligand-independent dimerization and activation of RET, and kinase domains mutations (primarily M918T, A883F or V804L/M) which promote RET auto-activation and consequent oncogenic signaling (Romei C et al., *Nat Rev Endocrinol.* 12(4):192-202 (2016 Apr.)).

Both PTC and MTC are treated with surgery when localized (Fagin J A & Wells S A Jr., *N Engl J Med.* 375(11):1054-67 (2016 Sep. 15)). Ablative therapy with radioactive iodine (RAI) is effective in PTC patients with recurrence; however, patients eventually become refractory to RAI. As MTC arises from follicular C-cells, RAI is not effective. Once advanced, RAI-refractory PTC and MTC are poorly responsive to chemotherapy and systemic treatment with a small molecule MKI is the standard of care for both. Sorafenib and lenvatinib are approved MKIs for progressive and/or symptomatic RAI-refractory PTC. Cabozantinib and vandetanib are approved MKIs for advanced MTC and are used regardless of RET mutational status. MKIs used to treat thyroid cancer have broad activity against many kinases (e.g., RAF, MET, EGFR, VEGFR1-3, PDGFR, RET and others), and are associated with significant dermatologic, cardiovascular, and gastrointestinal side effects. Therefore, National Clinical Practice Guidelines in Oncology from the National Comprehensive Cancer Network (available at https://www.nccn.org/professionals/physician_gls/f_guidelines.asp) recommends careful monitoring and dose interruption and/or dose modification for drug-related side effects with these agents. For patients with disease progression on MKI therapy or MKI intolerance, there are no effective therapies and NCCN guidelines recommend clinical trial participation.

Given the strong genetic and preclinical evidence that activated RET is an oncogenic disease driver, the lack of selective RET inhibitors available, and the poor prognosis of many patients with RET-altered tumors, a need remains for identifying dosing amounts and schedules with the appropriate safety, exposures, and tolerability for selective RET inhibitors for the treatment of RET-altered cancers.

Small molecule compounds that selectively inhibit RET are a desirable means for treating cancers having an activating RET alteration. One small molecule is (1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexanecarboxamide (Compound 1). Compound 1 has the chemical structure:

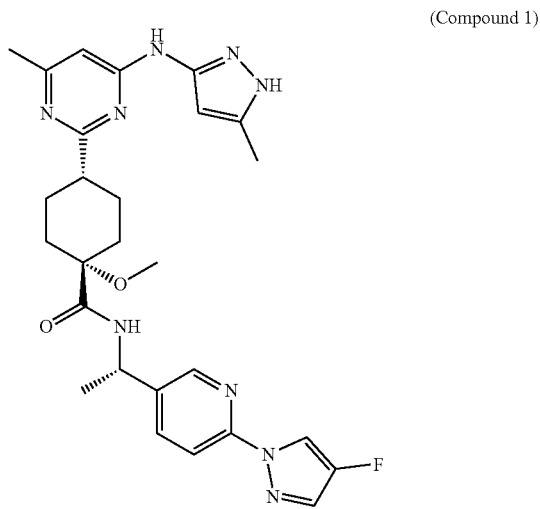 [SMILES: CO[C@]1(C(=O)N[C@@H](C)c2ccc(-n3cc(F)cn3)nc2)CC[C@H](c2nc(C)cc(Nc3cc(C)[nH]n3)n2)CC1]

(Compound 1)

In Mar. 2017, Compound 1 (also known as BLU-667) entered Phase I clinical trials in the United States for the treatment of patients with thyroid cancer, non-small cell lung cancer, and other advanced solid tumors (NCT03037385). WO 2017/079140, incorporated herein by reference, describes the synthesis of Compound 1 (Example Compound 130) and also discloses the therapeutic activity of this molecule to inhibit, regulate, and/or modulate RET kinase (Assays, Example 10 on pp. 72-74).

ABBREVIATIONS AND DEFINITIONS

Figure 1A:
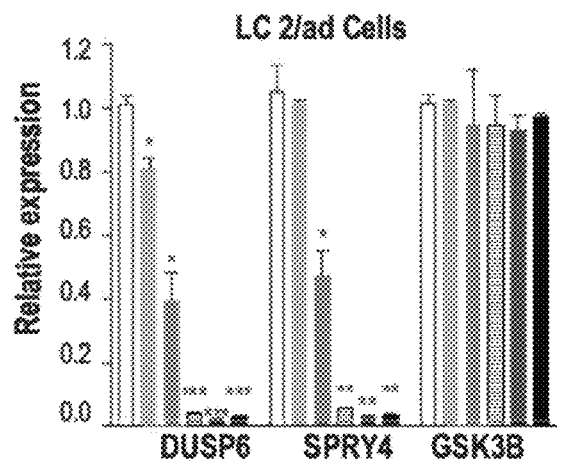
FIGS. 1A, 1B, and 1C are a series of bar graphs which show the impact of Compound 1 on expression of DUSP6 and SPRY4 in LC2/ad (FIG. 1A), MZ-CRC-1 (FIG. 1B), and TT (FIG. 1C) cells.

The following abbreviations and terms have the indicated means throughout:

"Compound 1" is (1S,4R)—N—((S)-1-(6-(4-fluoro-1H-pyrazol-1-yl)pyridine-3-yl)ethyl)-1-methoxy-4-(4-methyl-6-((5-methyl-1H-pyrazol-3-yl)amino)pyrimidin-2-yl)cyclohexanecarboxamide:

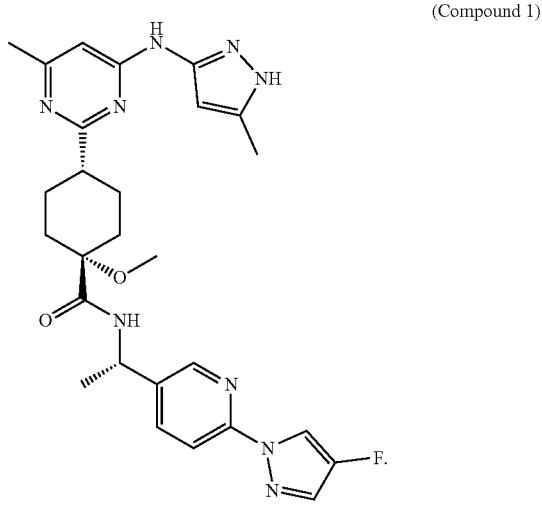 [SMILES: CO[C@]1(C(=O)N[C@@H](C)c2ccc(-n3cc(F)cn3)nc2)CC[C@H](c2nc(C)cc(Nc3cc(C)[nH]n3)n2)CC1]

(Compound 1)

As used herein, "DOR" means duration of response.
As used herein, "PD" means progressive disease.
As used herein, "SD" means stable disease.
As used herein, "CR" means complete response.
As used herein, "ORR" means overall all response rate.
As used herein, "CBR" means clinical benefit rate.
As used herein, "PFS" means progression free survival.
As used herein, a "fusion" is a protein that results from a chromosomal translocation in which two genes are joined with an in-frame coding sequence and results in a chimeric protein. In some embodiments, a fusion is a chromosomal translocation where the kinase domain of one protein fuses to a dimerization domain of another gene.

As used herein, a "RET-altered cancer" is a cancer having an activating rearranged during transfection (RET) alteration, which drives tumorigenesis. Non-limiting examples of activating RET alterations include mutations, fusions, and copy number variations.

As used herein, a "RET fusion" is a gene rearrangement. RET rearrangements create a fusion protein juxtaposing the RET kinase domain and a dimerization domain of another protein, creating a constitutively activated dimer, which drives tumorigenesis.

As used herein, a "RET fusion protein" is the result of a gene rearrangement.

As used herein, a "RET activating mutation" means a mutation in RET kinase which promotes ligand-independent, constitutive RET kinase activation, which drives tumorigenesis. For example, RET mutations can occur in the extracellular cysteine residues (e.g., C620R or C634R/W), which trigger aberrant receptor dimerization, or RET mutations can occur in the intracellular kinase domain.

As used herein, a "RET inhibitor" is a compound which inhibits the activity of RET kinase. RET kinase is wild-type RET kinase and/or one or more RET-altered kinases (e.g., RET fusion, RET mutation, or RET copy number variation).

Examples of RET inhibitors include, but are not limited to, Compound 1, LOXO-292 (selpercatinib), cabozantinib, vandetanib, alectinib, sorafenib, levatinib, ponatinib, dovitinib, sunitinib, foretinib, sitravatinib, DS-5010 (BOS172738), and RXDX-105.

In some embodiments, a RET inhibitor may also inhibit other kinases. As used herein, a "multi-kinase RET inhibitor" is a compound which inhibits wild type RET kinase and inhibits at least one other kinase equally or more potently than wild type RET kinase. Examples of multikinase RET inhibitors include: cabozantinib; vandetanib; alectinib; sorafenib; levatinib; ponatinib; dovitinib; sunitinib; foretinib; sitravatinib; DS-5010; and RXDX-105.

As used herein, the term "selective RET inhibitor" means a compound which selectively inhibits RET kinase. RET kinase can include RET wild type kinase and/or one or more RET-altered kinases (e.g., RET fusion, RET mutation, or RET copy number variation). A selective RET inhibitor's inhibitory activity against RET kinase is more potent in terms of $IC_{50}$ value (i.e., the $IC_{50}$ value is subnanomolar) when compared with its inhibitory activity against many other kinases (e.g., KDR, VEGFR-2, ABL, EGFR, FGFR2, HER2, IGFIR, JAKI, KIT, MET, AKTI, MEK1). Potency can be measured using known biochemical assays. Examples of selective RET inhibitors include Compound 1 and selpercatinib.

As used herein, the term "subject" or "patient" refers to organisms to be treated by the methods of the present disclosure. Such organisms include, but are not limited to, mammals (e.g., murines, simians, equines, bovines, porcines, canines, felines, and the like), and in some embodiments, humans.

Many cancers have been linked to aberrant RET expression (Kato et al., *Clin. Cancer Res.* 23(8):1988-97 (2017)). Non-limiting examples of "cancer" as used herein include lung cancer, head and neck cancer, gastrointestinal cancer, breast cancer, skin cancer, genitourinary tract cancer, gynecological cancer, hematological cancer, central nervous system (CNS) cancer, peripheral nervous system cancer, endometrial cancer, colorectal cancer, bone cancer, sarcoma, spitzoid neoplasm, adenosquamous carcinoma, pheochromocytoma (PCC), hepatocellular carcinoma, multiple endocrine neoplasia (MEN2A and MEN2B), and inflammatory myofibroblastic tumor. For other examples, see Nature Reviews Cancer 14:173-86 (2014).

Additional non-limiting examples of cancer include hemangiopericytoma, differentiated thyroid carcinoma, anaplastic thyroid carcinoma, lung carcinosarcoma, ureter urothelial carcinoma, uterine carcinosarcoma, basal cell carcinoma, Merkel cell carcinoma, atypical lung carcinoma, fallopian tube adenocarcinoma, ovarian epithelial carcinoma, salivary gland adenocarcinoma, meningioma, duodenal adenocarcinoma, cervical adenocarcinoma, adrenal carcinoma, gastroesophageal junction carcinoma, cutaneous squamous cell carcinoma, pancreatic ductal adenocarcinoma, prostate adenocarcinoma, esophageal adenocarcinoma, endometrial adenocarcinoma, ovarian serous carcinoma, carcinoma unknown primary, bladder urothelial (transition cell) carcinoma, lung squamous cell carcinoma, colorectal adenocarcinoma, head and neck squamous cell carcinoma, and gastric adenocarcinoma.

In some embodiments, the cancer is liver cholangiocarcinoma. In some embodiments, the cancer is duodenum adenocarcinoma. In some embodiments, the cancer is uterus endometrial adenocarcinoma endometrioid.

In some embodiments, MEN2A is associated with pheochromocytoma and parathyroid hyperplasia.

In some embodiments, MEN2B is associated with mucosal neuromas, pheochromocytomas, intestinal ganglioneuromas and marfanoid habitus.

In some embodiments, the lung cancer is chosen from small cell lung cancer (SCLC), lung adenocarcinoma, non-small cell lung cancer (NSCLC), bronchioles lung cell carcinoma, and mesothelioma. In some embodiments, the lung cancer is SCLC. In some embodiments, the lung cancer is NSCLC.

In some embodiments, the head and neck cancer is chosen from thyroid cancer and cancer of the salivary gland. In some embodiments, the thyroid cancer is chosen from papillary thyroid carcinoma (PTC), metastatic papillary thyroid cancer, medullary thyroid cancer (MTC), diffuse sclerosing variant of papillary thyroid cancer, and thyroid gland carcinoma. In some embodiments, the cancer is familial medullary thyroid cancer. In some embodiments, the thyroid cancer is PTC. In some embodiments, the thyroid cancer is MTC.

In some embodiments, the gastrointestinal cancer is chosen from esophageal cancer, esophagogastric cancer, gastrointestinal stromal tumor (e.g., imatinib-resistant gastrointestinal stromal tumor), small bowel cancer, diffuse gastric cancer, and ampullary carcinoma.

In some embodiments, the breast cancer is metastatic breast cancer. In some embodiments, skin cancer is melanoma or non-melanoma.

In some embodiments, the genitourinary tract cancer is chosen from colon cancer, metastatic colon cancer, bladder cancer, renal cell carcinoma (RCC), prostate cancer, hepatobiliary cancer, intrahepatic bile duct cancer, adrenocortical carcinoma, pancreatic cancer, and pancreatic ductal adenocarcinoma.

In some embodiments, the gynecological cancer is chosen from uterine sarcoma, germ cell tumor, cervical cancer, rectal cancer, testicular cancer, and ovarian cancer. In some embodiments, the hematological cancer is chosen from leukemia, primary myelofibrosis with secondary acute myeloid leukemia, myelodysplasia (MDS), non-Hodgkin lymphoma, chronic myeloid leukemia, Philadelphia chromosome-positive acute lymphoblastic leukemia, and chronic myelomonocytic leukemia (CMML).

In some embodiments, the peripheral nervous system cancer is paraganglioma. In some embodiments, the endometrial cancer is endometrial adenocarcinoma. In some embodiments, the sarcoma is a soft tissue sarcoma.

In some embodiments, the central nervous system (CNS) cancer is chosen from brain cancer associated with lung cancer and glioma.

Lung cancer is known to spread to the brain in about 40 percent of cases in which a metastasis has occurred. With lung cancer, this is considered stage 4 of the disease, and the average survival time with brain metastases is usually less than a year. Lung cancers with metastases to the brain have a relatively poor prognosis, e.g., chemotherapy drugs. Brain metastases are difficult to treat for many reasons. Often, by the time the patient first exhibits symptoms, they already have multiple lesions. Brain metastases tend to be very aggressive. The brain has many defenses to reduce the penetration of harmful substances. Specifically, the blood-brain-barrier prevents many medications, e.g., compounds from entering the brain. Treatment options may damage surrounding normal tissue and have a significant impact on the quality of life. In particular, there is a need to provide compounds that can be administered at a safe dose, with good tolerability, and which penetrate the brain for treatment of brain metastases.

In some embodiments, the cancer is brain metastasis associated with lung cancer.

In some embodiments, the cancer is a "RET-altered cancer," which, as used herein, means the cancer has an activating RET alteration. In some embodiments, the RET-altered cancer has a RET mutation or a RET gene rearrangement. In some embodiments, the RET-altered cancer is a RET-altered solid tumor.

As used herein, the term "effective amount" refers to the amount of a selective RET inhibitor (e.g., Compound 1 or a pharmaceutically acceptable salt thereof) sufficient to effect beneficial or desired results. Beneficial or desired results may be a therapeutic benefit or result or a physiological benefit or result. An effective amount can be administered in one or more administrations, applications, or dosages and is not intended to be limited to a specific formulation or administration route.

As used herein, the term "therapeutically effective amount" refers to the amount of a selective inhibitor (e.g., Compound 1 or a pharmaceutically acceptable salt thereof) sufficient to effect beneficial or desired therapeutic results in a subject. A therapeutically effective amount can be administered to a subject in need thereof in one or more administrations, applications, or dosages and is not intended to be limited to a specific formulation or administration route. In some embodiments, a therapeutically effective amount provides the desired safety, exposure, and tolerability. Selecting the therapeutically effective amount, i.e., the right dose for administering a compound, is a required step in the development of a pharmaceutical drug for clinical use. Without adequate information on dosage, it is not possible for doctors to prescribe a particular drug to patients. Therefore, determining the correct drug dosage is a key question that can only be answered in clinical studies. If the dose and frequency of administration that allows safe and predictable administration cannot be identified, then the compound cannot be a medically useful or commercially viable pharmaceutical product.

As used herein, the term "physiologically effective amount" refers to the amount of a selective inhibitor (e.g., Compound 1 or a pharmaceutically acceptable salt thereof) sufficient to effect beneficial or desired physiological result in a subject. A physiological result may be a sustained down-regulation of at least one effect marker in the subject.

As used herein, the term "treating" includes any effect, e.g., lessening, reducing, modulating, ameliorating, or eliminating, that results in the improvement of the condition, disease, disorder, and the like, or ameliorating a symptom thereof.

As used herein, an "effect marker" means DUSP6 mRNA expression, SPRY4 mRNA expression, CEA, calcitonin, KIF5B ctDNA or TP53 ctDNA.

Some example embodiments of the disclosure include the following:

1. A method of treating a subject afflicted with a cancer having an activating rearranged during transfection (RET) alteration, the method comprising administering to the subject a therapeutically effective amount of 300 to 400 mg of Compound 1 or a pharmaceutically acceptable salt thereof once daily.
2. The method of embodiment 1, wherein the amount administered is 300 mg.
3. The method of embodiment 1 or 2, wherein the amount administered is 400 mg.
4. The method of any one of embodiments 1-3, wherein the cancer is chosen from papillary thyroid carcinoma (PTC), medullary thyroid cancer (MTC), pheochromocytoma (PCC), pancreatic ductal adenocarcinoma, multiple endocrine neoplasia (MEN2A and MEN2B), metastatic breast cancer, testicular cancer, small cell lung cancer, non-small cell lung cancer (NSCLC), chronic myelomonocytic leukemia (CMML), colorectal cancer, ovarian cancer, inflammatory myofibroblastic tumor, and cancer of the salivary gland.
5. The method of any one of embodiments 1-3, wherein the cancer is chosen from esophageal cancer, skin cancer (non-melanoma), endometrial cancer, head and neck cancer, bladder cancer, prostate cancer, hematological cancer, leukemia, soft tissue sarcoma, renal cell carcinoma (RCC), non-Hodgkin lymphoma, hepatobiliary cancer, adrenocortical carcinoma, myelodysplasia (MDS), uterine sarcoma, germ cell tumor, cervical cancer, central nervous system cancer, bone cancer, ampullary carcinoma, gastrointestinal stromal tumor, small bowel cancer, mesothelioma, rectal cancer, paraganglioma, and intrahepatic bile duct cancer.
6. The method of any one of embodiments 1-3, wherein the cancer is chosen from adenocarcinoma, spitzoid neoplasm, lung adenocarcinoma, adenosquamous carcinoma, colon cancer, metastatic colon cancer, metastatic papillary thyroid cancer, diffuse sclerosing variant of papillary thyroid cancer, primary myelofibrosis with secondary acute myeloid leukemia, diffuse gastric cancer, thyroid gland carcinoma, and bronchioles lung cell carcinoma.
7. The method of any one of embodiments 1-3, wherein the cancer is chosen from hepatobiliary cancer, ampullary carcinoma, small bowel cancer, intrahepatic bile duct cancer, metastatic colon cancer, brain cancer associated with lung cancer, brain metastasis associated with lung cancer, and retropentoneal paraganglioma.
8. The method of any one of embodiments 1-3, wherein the cancer is chosen from medullary thyroid cancer (MTC) and non-small cell lung cancer (NSCLC).
9. The method of embodiment 8, wherein the cancer is chosen from sporadic MTC, metastatic RET-altered NSCLC, tyrosine kinase inhibitor (TKI)-refractory KIF5B-RET NSCLC, and KIF5B-RET NSCLC.
10. The method of any one of embodiments 1-3, wherein the cancer is chosen from a brain cancer associated with a lung cancer.
11. The method of embodiment 10, wherein the brain cancer is brain metastasis.
12. The method of any one of embodiments 1-11, wherein the activating RET alteration comprises a RET mutation or a RET gene rearrangement (fusion).
13. The method of any one of embodiments 1-11, wherein the activating RET alteration is a RET mutation.
14. The method of embodiment 12 or 13, wherein the RET mutation is a point mutation.
15. The method of any one of embodiments 12-14, wherein the RET mutation is a resistance mutation.
16. The method of any one of embodiments 12-15, wherein the RET alteration is a RET mutation chosen from Table 1.
17. The method of any one of embodiments 12-16, wherein the RET mutation is V804M, M918T, C634R, or C634W.
18. The method of any one of embodiments 1-4, 8, 9, and 12-16, wherein the cancer is RET-altered medullary thyroid cancer (MTC).
19. The method of embodiment 18, wherein the cancer is familial MTC.
20. The method of embodiment 18, wherein the cancer is sporadic MTC.
21. The method of any one of embodiments 1-3 and 12-19, wherein the cancer is MTC having a M918T mutation.
22. The method of any one of embodiments 1-3 and 12-19, wherein the cancer is MTC having a C634R mutation.
23. The method of any one of embodiments 1-3 and 12-19, wherein the cancer is MTC having a V804M mutation.
24. The method of any one of embodiments 1-3, 6, and 12-16, wherein the cancer is paraganglioma.
25. The method of embodiment 24, wherein the cancer is retropentoneal paraganglioma.
26. The method of any one of embodiments 1-3, 6, 12-16, 24, and 25, wherein the paraganglioma has a R77H mutation.
27. The method of any one of embodiments 1-11, wherein the activating RET alteration is a gene-rearrangement (fusion).
28. The method of embodiment 27, wherein the activating RET alteration is a fusion with a RET fusion partner chosen from Table 2.
29. The method of embodiment 27 or 28, wherein the fusion is KIF5B-RET, CCDC6-RET, KIAA1468-RET, or NCOA4-RET.
30. The method of any one of embodiments 1-4 and 27-29, wherein the cancer is RET-altered NSCLC.
31. The method of embodiment 30, wherein the cancer is NSCLC having a KIF5B-RET fusion.
32. The method of embodiment 30, wherein the cancer is NSCLC having a CCDC6-RET fusion.
33. The method of embodiment 30, wherein the cancer is NSCLC having a KIAA1468-RET fusion.
34. The method of embodiment 30, wherein the cancer is NSCLC having a RET fusion identified as FISH positive.
35. The method of embodiment 29 or 30, wherein the RET alteration is KIF5B-RET V804L (cabozantinib resistant).
36. The method of embodiment 29 or 30, wherein the RET alteration is CCDC6-RET V804M (ponatinib resistant).
37. The method of any one of embodiments 1-4 and 27-29, wherein the cancer is RET-altered PTC.
38. The method of embodiment 37, wherein the cancer is PTC having a CCDC6-RET fusion.
39. The method of embodiment 37, wherein the cancer is PTC having a NCOA4-RET fusion.
40. The method of any one of embodiments 1-3 and 27-29, wherein the cancer is RET-altered intrahepatic bile duct carcinoma.
41. The method of embodiment 40, wherein the cancer is intrahepatic bile duct carcinoma having a NCOA4-RET fusion.
42. The method of any one of embodiments 1-41, wherein the subject has not received prior treatment with a multikinase RET inhibitor.
43. The method of any one of embodiments 1-41 wherein the subject has received one or more prior treatments with a multikinase RET inhibitor.
44. The method of embodiment 43, wherein the multikinase RET inhibitor is chosen from lenvatinib, vandetanib, cabozantinib, and RXDX-105.

45. The method of any one of embodiments 1-41, wherein the subject has not received prior treatment with platinum.
46. The method of any one of embodiments 1-41, wherein the subject has received prior treatment with platinum.
47. The method of any one of embodiments 1-41, wherein the subject has received prior treatment with a selective RET inhibitor.
48. The method of any one of embodiments 1-47, wherein the subject has not received prior chemotherapy.
49. The method of any one of embodiments 1-47, wherein the subject has received prior chemotherapy.
50. The method of embodiment 49, wherein the prior chemotherapy is chosen from carboplatin, pemetrexed, abraxane, cisplatin, bevacizumab, and combinations thereof.
51. The method of any one of embodiments 1-42, wherein the subject has not received prior immunotherapy.
52. The method of any one of embodiments 1-42, wherein the subject has received prior immunotherapy.
53. The method of embodiment 52, wherein the prior immunotherapy is chosen from ipilimumab, pembrolizumab, nivolumab, MPDL3280A, MEDI4736, and combinations thereof.
54. A method of treating a subject afflicted with a brain cancer associated with a RET-altered lung cancer, the method comprising administering to the subject a therapeutically effective amount of Compound 1 or a pharmaceutically acceptable salt thereof.
55. The method of embodiment 54, wherein the brain cancer is brain metastasis.
56. A method of treating a subject afflicted with a cancer having an activating RET mutation, the comprising administering to the subject a physiologically effective amount of a RET inhibitor, wherein administration of the RET inhibitor is associated with a sustained down-regulation of at least one effect marker in the subject.
57. The method of embodiment 56, wherein the RET inhibitor is orally administered.
58. The method of embodiment 56 or 57, wherein the RET inhibitor is Compound 1 or a pharmaceutically acceptable salt thereof.
59. The method of any one of embodiments 56-58, wherein the effect marker is chosen from DUSP6 mRNA expression, SPRY4 mRNA expression, carcinoembryonic antigen level, and calcitonin level.
60. The method of any one of embodiments 56-58, wherein the effect marker is KIF5B ctDNA level or TP53 ctDNA level.
61. The method of any one of embodiments 56-59, wherein the amount administered to the subject produces a greater than 95% down-regulation of at least one effect marker.
62. The method of any one of embodiments 56-59, wherein the amount administered to the subject produces a greater than 94%, greater than 93%, greater than 92%, greater than 91%, greater than 90%, greater than 89%, greater than 88%, greater than 87%, greater than 86% greater than 85%, greater than 80%, greater than 75%, greater than 70%, greater than 65%, greater than 60%, greater than 55%, or greater than 50% down-regulation in at least one effect marker.
63. The method of embodiment 61, wherein the amount administered to the subject produces a greater than 89%, greater than 88%, greater than 87%, greater than 86%, greater than 85%, greater than 80%, greater than 75%, or greater than 70% down-regulation in at least one effect marker.
64. The method of any one of embodiments 56-59, wherein at least two effect markers are down-regulated.

TABLE 1

RET Point Mutations.

| Example RET Point Mutation | Example RET Point Mutation |
|---|---|
| Amino acid position 2 | Amino acid position 665 (e.g., H665Q) |
| Amino acid position 3 | Amino acid position 666 (e.g., K666E, K666M, or K666N) |
| Amino acid position 4 | Amino acid position 686 (e.g., S686N) |
| Amino acid position 5 | Amino acid position 691 (e.g., G691S) |
| Amino acid position 6 | Amino acid position 694 (e.g., R694Q) |
| Amino acid position 7 | Amino acid position 700 (e.g., M700L) |
| Amino acid position 8 | Amino acid position 706 (e.g., V706M or V706A) |
| Amino acid position 11 | Amino acid position 713 splice variant (e.g., E713K) |
| Amino acid position 12 | Amino acid position 736 (e.g., G736R) |
| Amino acid position 13 | Amino acid position 748 (e.g., G748C) |
| Amino acid position 20 | Amino acid position 750 (e.g., A750P) |
| Amino acid position 32 (e.g., S32L) | Amino acid position 765 (e.g., S765P) |
| Amino acid position 34 (e.g., D34S) | Amino acid position 766 (e.g., P766S or P766M6) |
| Amino acid position 40 (e.g., L40P) | Amino acid position 768 (e.g., E768Q or E768D) |
| Amino acid position 64 (e.g., P64L) | Amino acid position 769 (e.g., L769L) |
| Amino acid position 67 (e.g., R67H) | Amino acid position 770 (e.g., R770Q) |
| Amino acid position 114 (e.g., R114H) | Amino acid position 771 (e.g., D771N) |
| Amino acid position 136 (e.g., glutamic acid to stop codon) | Amino acid position 777 (e.g., N777S) |
| Amino acid position 145 (e.g., V145G) | Amino acid position 778 (e.g., V778I) |
| Amino acid position 180 (e.g., arginine to stop codon) | Amino acid position 781 (e.g., Q781R) |
| Amino acid position 200 | Amino acid position 790 (e.g., L790F) |
| Amino acid position 292 (e.g., V292M) | Amino acid position 791 (e.g., Y791F or Y791N) |
| Amino acid position 294 | Amino acid position 802 |
| Amino acid position 321 (e.g., G321R) | Amino acid position 804 (e.g., V804L, V804M, V804M, or V804E) |

TABLE 1-continued

RET Point Mutations.

| Example RET Point Mutation | Example RET Point Mutation |
|---|---|
| Amino acid position 330 (e.g., R330Q) | Amino acid position 805 (e.g., E805K) |
| Amino acid position 338 (e.g., T338I) | Amino acid position 806 (e.g., E806C, Y806E, Y806F, Y806S, Y806G, Y806H, Y806N, or Y806C) |
| Amino acid position 360 (e.g., R360W) | Amino acid position 818 (e.g., E818K) |
| Amino acid position 373 (e.g., alanine to frameshift) | Amino acid position 819 (e.g., S819I) |
| Amino acid position 388 (e.g., V388A) | |
| Amino acid position 393 (e.g., F393L) | Amino acid position 823 (e.g., G823E) |
| Amino acid position 432 | Amino acid position 826 (e.g., Y826M) |
| Δ Amino acid residues 505-506 (6-Base Pair In-Frame Germline Deletion in Exon 7) | Amino acid position 833 (e.g., R833C) |
| Amino acid position 510 (e.g., A510V) | Amino acid position 841 (e.g., P841L or P841P) |
| Amino acid position 511 (e.g., E511K) | Amino acid position 843 (e.g., E843D) |
| Amino acid position 513 (e.g., A513D) | Amino acid position 844 (e.g., R844W, R844Q, or R844L) |
| Amino acid position 515 (e.g., C515S, C515W) | Amino acid position 848 (e.g., M848T) |
| Amino acid position 525 (e.g., R525W) | Amino acid position 852 (e.g., I852M) |
| Amino acid position 531 (e.g., C531R, or 9 base pair duplication) | Amino acid position 866 (e.g., A866W) |
| Amino acid position 532 (e.g., duplication) | Amino acid position 873 (e.g., R873W) |
| Amino acid position 533 (e.g., G533C or G533S) | Amino acid position 876 (e.g., A876V) |
| Amino acid position 550 (e.g., G550E) | Amino acid position 881 (e.g., L881V) |
| Amino acid position 591 (e.g., V591I) | Amino acid position 882 |
| Amino acid position 593 (e.g., G593E) | Amino acid position 883 (e.g., A883F, A883S, A883T, or A883T*) |
| Amino acid position 600 (e.g., R600Q) | Amino acid position 884 (e.g., E884K) |
| Amino acid position 602 (e.g., I602V) | Amino acid position 886 (e.g., R886W) |
| Amino acid position 603 (e.g., K603Q or K603E2) | Amino acid position 891 (e.g., S891A) |
| Amino acid position 606 (e.g., Y606C) | Amino acid position 897 (e.g., R897Q) |
| Amino acid position 609 (e.g., C609Y, C609S, C609G, C609R, C609F, or C609W) | Amino acid position 898 (e.g., D898V) |
| Amino acid position 611 (e.g., C611R, C611S, C611G, C611Y, C611F, or C611W) | Amino acid position 901 (e.g., E901K) |
| Amino acid position 618 (e.g., C618S, C618Y, C618R, C618Y, C618G, C618F, C618W) | Amino acid position 904 (e.g., S904F or S904C2) |
| Amino acid position 619 (e.g., F619F) | Amino acid position 907 (e.g., K907E or K907M) |
| Amino acid position 620 (e.g., C620S, C620W, C620R, C620G, C620L, C620Y, C620F) | Amino acid position 908 (e.g., R908K) |
| Amino acid position 623 (e.g., E623K) | Amino acid position 911 (e.g., G911D) |
| Amino acid position 624 (e.g., D624N) | Amino acid position 912 (e.g., R912P, R912Q) |
| Amino acid position 629 (e.g., L629P) | |
| Amino acid position 630 (e.g., C630A, C630R, C630S, C630Y, or C630F) | Amino acid position 918 (e.g., M918T, M918V, or M918L6) |
| Amino acid position 631 (e.g., D631N, D631Y, D631A, D631G, D631V, or D631E, D631_R635DELINSG) | Amino acid position 919 (e.g., A919V) |
| Amino acid position 632 (e.g., E632K or E632G5) | Amino acid position 921 (e.g., E921K) |
| Δ Amino acid residues 632-633 (6-Base Pair In-Frame Germline Deletion in Exon 11) | Amino acid position 922 (e.g., S922P or S922Y) |
| Amino acid position 633 (e.g., 9 base pair duplication) | Amino acid position 930 (e.g., T930M) |
| Amino acid position 634 (e.g., C634W, C634Y, C634S, C634R, C634F, C634G, C634L, C634A, or C634T, or an insertion ELCR2, or a 12 base pair duplication) | Amino acid position 961 (e.g., F961L) |
| Amino acid position 635 (e.g., R635G) | Amino acid position 972 (e.g., R972G) |
| Amino acid position 636 (e.g., T636P or T636M4) | Amino acid position 982 (e.g., R982C) |
| Amino acid position 637 (e.g., V637R) | |
| Amino acid position 640 (e.g., A640G) | Amino acid position 1009 (e.g., M1009V) |
| Amino acid position 641 (e.g., A641S or A641T8) | Amino acid position 1017 (e.g., D1017N) |
| Amino acid position 648 (e.g., V648I) | Amino acid position 1041 (e.g., V1041G) |
| Amino acid position 649 (e.g., S649L) | Amino acid position 1064 (e.g., M1064T) |
| Amino acid position 664 (e.g., A664D) | RET + 3 |
| Amino acid position 629 (e.g., L629P) | Amino acid position 637 (e.g., V637R) |

Some of the RET point mutations in Table 1 are discussed in: U.S. Patent Application Publication No. 2014/0272951; Krampitz et al., *Cancer* 120:1920-31 (2014); Latteyer et al., *J Clin. Endocrinol. Metab.* 101(3): 1016-22 (2016); Silva et al. *Endocrine* 49.2:366-72 (2015); Jovanovic et al., *Prilozi* 36(1):93-107 (2015); Qi et al., *Oncotarget* 6(32):33993-4003 (2015); Kim et al. ACTA ENDOCRINOLOGICA-BUCHAREST 11.2, 189-194, (2015); Cecchirini et al. *Oncogene*, 14:2609-12 (1997); Karrasch et al., *Eur. Thyroid J* 5(1):73-77 (2016); Scollo et al., *Endocr. J* 63:87-91 (2016); and Wells et al., *Thyroid* 25:567-610 (2015).

R525W and A513D may act in combination with S891A to enhance oncogenic

TABLE 2

RET Fusions.

| RET fusion partner | Exemplary cancers in which the fusion is found |
|---|---|
| BCR | Chronic Myelomonocytic Leukemia (CMML) |
| CLIP 1 | Adenocarcinoma |
| KIF5B | NSCLC, Ovarian Cancer, Spitzoid Neoplasm; Lung Adenocarcinoma, Adenosquamous Carcinomas |
| CCDC6 | NSCLC, Colon Cancer, Papillary Thyroid Cancer; Adenocarcinoma; Lung Adenocarcinoma; Metastatic Colorectal Cancer; Adenosquamous Carcinoma, Metastatic papillary thyroid cancer |
| PTClex9 | Metastatic papillary thyroid cancer |
| NCOA4 | Papillary Thyroid Cancer, NSCLC, Colon Cancer, Salivary Gland Cancer, Metastatic Colorectal Cancer; Lung Adenocarcinoma, Adenosquamous Carcinomas; Diffuse Sclerosing Variant of Papillary Thyroid Cancer |
| TRIM33 | NSCLC, Papillary Thyroid Cancer |
| ERC1 | Papillary Thyroid Cancer, Breast Cancer |
| FGFR1OP | CMML, Primary Myelofibrosis with secondary Acute Myeloid Leukemia |
| MBD1 | Papillary Thyroid Cancer |
| RAB61P2 | Papillary Thyroid Cancer |
| PRKAR1A | Papillary Thyroid Cancer |
| TRIM24 | Papillary Thyroid Cancer |
| KTN1 | Papillary Thyroid Cancer |
| GOLGA5 | Papillary Thyroid Cancer, Spitzoid Neoplasms |
| HOOK3 | Papillary Thyroid Cancer |
| KIAA1468 | Papillary Thyroid Cancer, Lung Adenocarcinoma |
| TRIM27 | Papillary Thyroid Cancer |
| AKAP13 | Papillary Thyroid Cancer |
| FKBP15 | Papillary Thyroid Cancer |
| SPECC1L | Papillary Thyroid Cancer, Thyroid Gland Carcinoma |
| TBL1XR1 | Papillary Thyroid Cancer, Thyroid Gland Carcinoma |
| CEP55 | Diffuse Gastric Cancer |
| CUX1 | Lung Adenocarcinoma |
| ACBD5 | Papillary Thyroid Carcinoma |
| MYH13 | Medullary Thyroid Carcinoma |
| PIBF1 | Bronchiolus Lung Cell Carcinoma |
| KIAA1217 | Papillary Thyroid Cancer, Lung Adenocarcinoma, NSCLC |
| MPRIP | NSCLC |

Some of the RET fusions in Table 2 are discussed in: Grubbs et al., *J Clin Endocrinol Metab*, 100:788-93 (2015); Halkova et al., *Human Pathology* 46:1962-69 (2015); U.S. Pat. Nos. 9,297,011; 9,216,172; Le Rolle et al., *Oncotarget* 6(30):28929-37 (2015); Antonescu et al., *Am J Surg Pathol* 39(7):957-67 (2015); U.S. Patent Application Publication No. 2015/0177246; U.S. Patent Application Publication No. 2015/0057335; Japanese Patent Application Publication No. 2015/109806A; Chinese Patent Application Publication No. 105255927A; Fang, et al., *Journal of Thoracic Oncology* 11.2 (2016): S21-S22; European Patent Application Publication No. EP3037547A1; Lee et al., *Oncotarget* DOI: 10.18632/oncotarget.9137, e-published ahead of printing, 2016; Saito et al., *Cancer Science* 107:713-20 (2016); Pirker et al., *Transl Lung Cancer Res*, 4(6):797-800 (2015); and Joung et al., *Histopathology* 69(1):45-53 (2016).

A person of ordinary skill in the art may determine if a subject possesses a RET-altered cell, cancer, gene, or gene product, e.g., having a mutation, e.g., a fusion, deletion, insertion, translocation, frameshift, duplication, point mutation, and/or rearrangement, e.g., using a method selected from hybridization-based methods, amplification-based methods, microarray analysis, flow cytometry analysis, DNA sequencing, next-generation sequencing (NGS), primer extension, PCR, in situ hybridization, fluorescent in situ hybridization, dot blot, and Southern blot.

To detect a fusion, primary tumor samples may be collected from a subject. The samples are processed, the nucleic acids are isolated using techniques known in the art, then the nucleic acids are sequenced using methods known in the art. Sequences are then mapped to individual exons, and measures of transcriptional expression (such as RPKM, or reads per kilobase per million reads mapped), are quantified. Raw sequences and exon array data are available from sources such as TCGA, ICGC, and the NCBI Gene Expression Omnibus (GEO). For a given sample, individual exon coordinates are annotated with gene identifier information, and exons belonging to kinase domains are flagged. The exon levels are then z-score normalized across all tumors samples.

Next, genes in which 5' exons are expressed at significantly different levels than 3' exons are identified. A sliding frame is used to identify the breakpoint within an individual sample. Specifically, at each iteration, an incremental breakpoint divides the gene into 5' and 3' regions, and a t-statistic is used to measure the difference in expression (if any) between the two regions. The breakpoint with the maximal t-statistic is chosen as the likely fusion breakpoint. As used herein, "breakpoint" is the boundary at which two different genes are fused. It is sometimes referred to as a "fusion point." The location where the difference in exon expression is maximal between 5' and 3' is the inferred breakpoint of the fusion. Thousands of tumor samples can be rapidly profiled in this manner, generating a list of fusion candidates (ranked by t-statistic). High-ranking candidates can then be validated, and fusion partners identified by examining the raw RNA-seq data sets, and identifying chimeric pairs and/or split reads which support the fusion. Candidate fusions can then be experimentally confirmed as described below.

Alternatively, the methods described in Wang L et al., *Genes Chromosomes Cancer* 51(2):127-39 (2012). doi: 10.1002/gcc.20937, Epub 2011 Oct. 27; and Suehara Y et al., *Clin Cancer Res.* 18(24):6599-608 (2012). doi: 10.1158/1078-0432.CCR-12-0838, Epub 2012 Oct. 10 can also be used.

It has been proposed that the inclusion of a pharmacodynamic assessment of molecularly targeted therapies in clinical trials can streamline the drug development process (Tan D S et al., *Cancer J* 15(5):406-20 (2009); Sarker D & Workman P. *Adv Cancer Res* 96:213-68 (2007)). Pharmacodynamic biomarkers have been successfully utilized for the clinical development of kinase inhibitors, including imatinib and gefitinib (Sarker D & Workman P. *Adv Cancer Res* 96:213-68 (2007); Baselga J et al., *J Clin Oncol* 23(23): 5323-33 (2005); Druker B J et al., *N Engl J Med* 344(14): 1031-7 (2001)). As described herein, Compound 1 dose-dependently inhibited RET and SHC activation, which mirrored the inhibition of DUSP6 and SPRY4 transcription across RET-driven preclinical models, indicating that these transcripts can serve as biomarkers for RET inhibitory activity. The translational capability of these markers was established in this study in which MTC tumor shrinkage induced by Compound 1 treatment was associated with efficient inhibition of DUSP6 and SPRY4 expression within the tumor tissue. To Applicant's knowledge, this represents the first confirmation of RET target engagement by a small molecule inhibitor, multi-targeted or selective, within the clinical setting. These effect markers may be used to more precisely define the optimal dose and schedule required for effective RET inhibition.

While it is possible for Compound 1 to be administered alone, in some embodiments, Compound 1 can be administered as a pharmaceutical formulation, wherein Compound 1 is combined with one or more pharmaceutically acceptable excipients or carriers. Compound 1 may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules, and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams, and gels may contain, in addition to an active compound, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an active compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Dosage forms for the topical or transdermal administration of Compound 1 include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

When Compound 1 is administered as a pharmaceutical, to humans and animals, it can be given per se or as a pharmaceutical composition containing, for example, 0.1 to 99.5% (such as 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

The present disclosure is further illustrated by the following examples which should not be construed as further limiting. The contents of all references cited throughout this application are expressly incorporated herein by reference.

EXAMPLES

Example 1: DUSP6 and SPRY4 Expression Analysis

Cells were treated with the indicated compounds for 7 hours before lysis with Buffer RLT (QIAGEN, Hilden, Germany) containing 1% β-mercaptoethanol. Total RNA was isolated using the Rneasy Plus Mini kit (QIAGEN, Hilden, Germany) according to the manufacturer's instructions. First-strand cDNA was synthesized using the SuperScript VILO Master Mix (Thermo Fisher Scientific, Waltham, MA) according to the manufacturer's instructions.

Figure 1B:
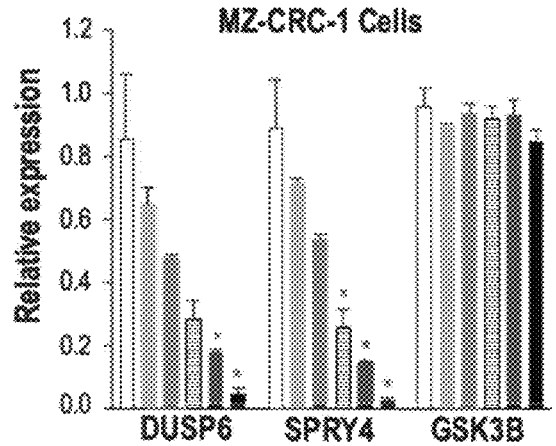
Figure 1C:
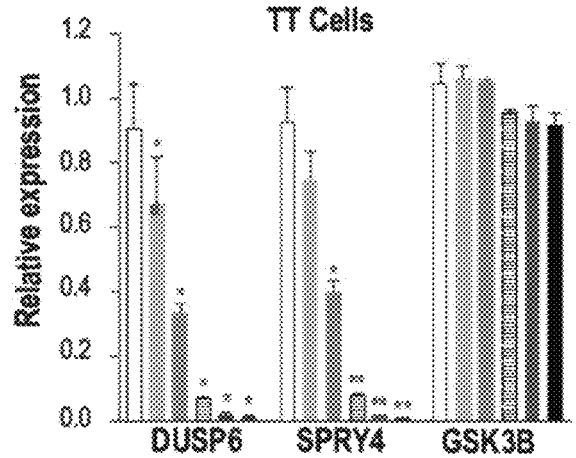
Figure 2:
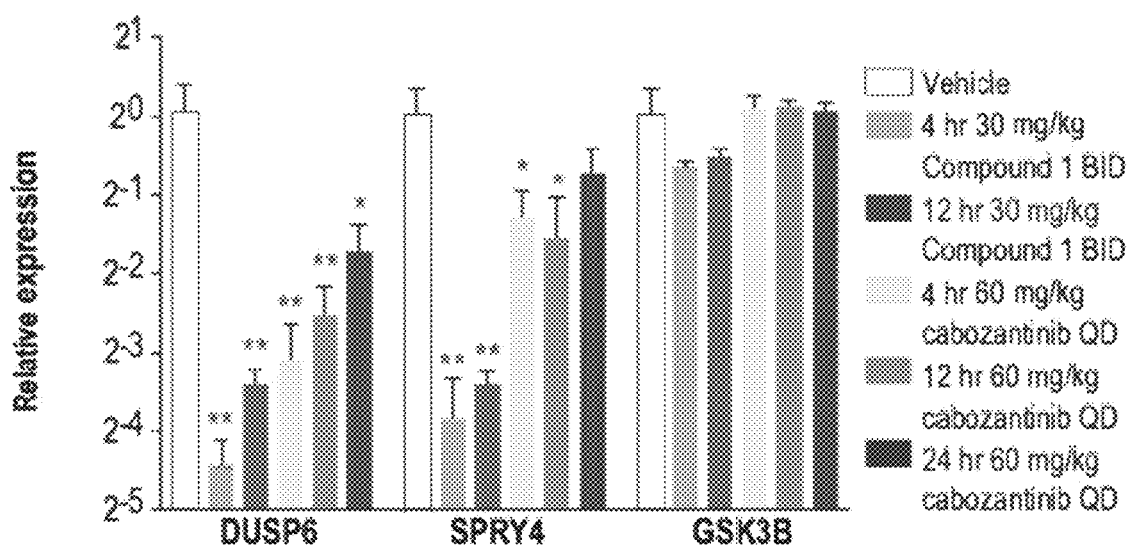
FIG. 2 is a bar graph which shows the sustained decrease in expression of the MAPK target genes DUSP6 and SPRY4 in a KIF5B-RET NSCLC PDX model.

Real-time qPCR was run on ViiA 7 Real Time PCR System (Thermo Fisher Scientific). For qRT-PCR, the expression of the reference gene glucuronidase beta (GUSB) was used to normalize expression of the target genes DUSP6, SPRY4, and glycogen synthase kinase 3 beta (GSK3B). Replicate qRT-PCR reactions were analyzed for each sample, and QuantStudio Real-Time PCR software (Life Technologies, Carlsbad, CA) normalized the average expression of DUSP6, SPRY4, or GSK3B to the average expression of the reference gene GUSB in each sample. FIGS. 1A-1C show relative transcript expression of RET pathway targets DUSP6 and SPRY4 and AKT-pathway target GSK3B 7 hours after treatment of L2C/ad cells (FIG. 1A), MZ-CRC-1 cells (FIG. 1B), or TT MTC cells (FIG. 1C) with Compound 1 or cabozantinib. FIG. 2 shows relative transcript expression of DUSP6, SPRY4 and GSK3B from KIF5B-RET NSCLC PDX. Tumors collected at the indicated times (hours) after administration of last dose. Data are the mean+ SD. *P<0.05, P<0.01, *P<0.001, 2-sided Student's t-test. SD, standard deviation.

Example 2: Generation of KIF5B-RET Ba/F3 Cells and ENU Mutagenesis Assays

Figure 3:
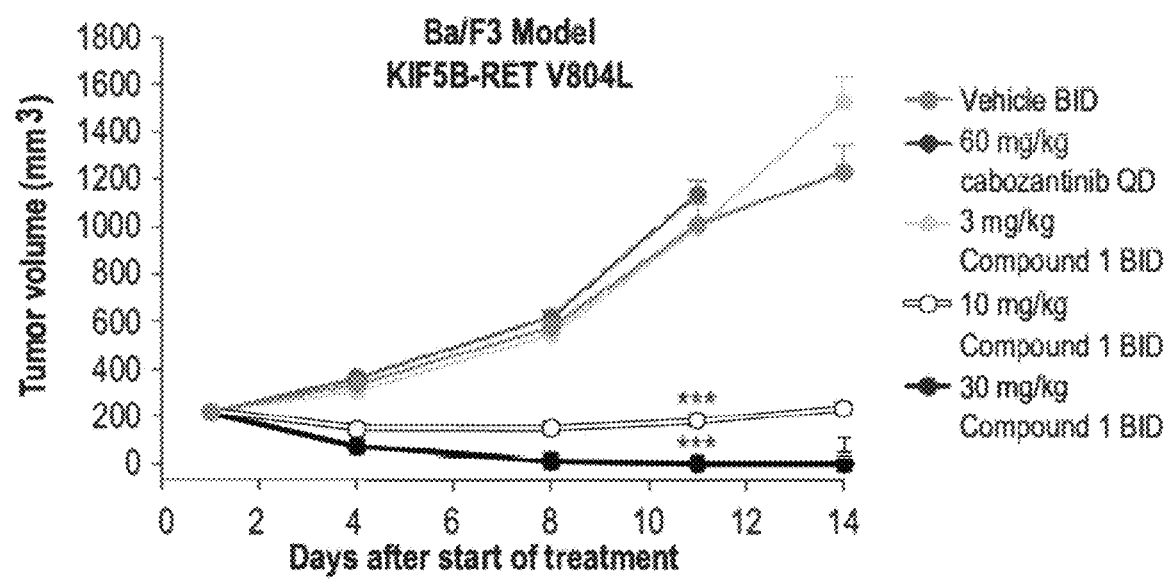
FIG. 3 is a graph which shows in vivo anti-tumor activity of Compound 1 in a cabozantinib-resistant tumor model generated from an engineered KIF5B-RET V804L cell line.

The DNA encoding the amino acid sequence of human KIF5B-RET variant 1 was placed in a lentivirus vector under a doxycycline-inducible promoter to maximize expression with a carboxyl-terminal FLAG epitope to facilitate immunodetection of the fusion by anti-FLAG antibodies. Lentiviral-mediated gene transduction was used to express KIF5B-RET in Ba/F3 cells, KIF5B-RET dependent cells were selected by IL-3 withdrawal and confirmed to express the KIF5B-RET fusion protein by immunoblot analysis. To generate Ba/F3 cells carrying V804 substitutions, WT KIF5B-RET Ba/F3 cells were mutagenized overnight with ENU and plated in 96-well plates for a period of 2 weeks in the presence of 6 concentrations of MKIs (ponatinib, regorafenib, cabozantinib, or vandetanib). The concentrations chosen ranged from 2×-64× the proliferation $IC_{50}$ for each compound: 125 nM to 4 µmol/L cabozantinib, 20 to 640 nM ponatinib, and 250 nM to 8 µmol/L vandetanib. Genomic DNA was isolated from resistant clones, and Sanger sequencing was used to identify those that harbored substitutions. FIG. 3 shows antitumor activity of Compound 1 compared with cabozantinib in KIF5B-RET V804L Ba/F3 allografts.

Example 3: Phase I Study

A phase I, first-in-human study (NCT03037385) to define the maximum tolerated dose, safety profile, pharmacokinetics, and preliminary anti-tumor activity of Compound 1 in advanced, RET-altered NSCLC, MTC and other solid tumors was initiated. Prior to study entry, written informed consent was obtained from all patients for treatment with Compound 1 and collection of blood and tumor samples for exploratory biomarker analyses to characterize potential predictive biomarkers of safety and efficacy. Adult patients (≥18 years of age) must have had advanced, unresectable solid tumors, with an Eastern Cooperative Oncology Group performance status of 0 to 2, and adequate bone marrow, hepatic, renal, and cardiac function. Compound 1 was administered orally, once daily, on a 4-week cycle using a Bayesian Optimal Interval Design. At dose levels≥120 mg, documented RET-alteration was additionally required for study entry. Adverse events were graded per Common Terminology Criteria for Adverse Events (CTCAE). Radiographic response by computed tomography was evaluated RECIST version 1.1 (*European Journal of Cancer* 45: 228-247 (2009)). Levels of ctDNA in plasma were assessed using the PlasmaSELECT™-R64 NGS panel (Personal Genome Diagnostics, Baltimore, MD). Serum calcitonin levels in MTC patients were measured by ELISA (Medpace, Cincinnati, OH). Tumor DUSP6/SPRY4 levels were analyzed by qRT-PCR (Molecular MD, Portland, OR).

Case Studies

Figure 4A:
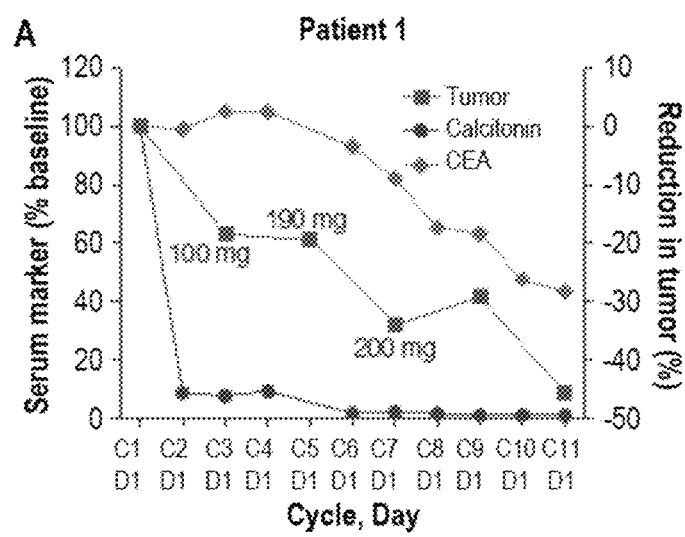
FIG. 4A is a graph which shows tumor size and levels of calcitonin and CEA (carcinoembryonic antigen) decrease over the course of treatment with Compound 1. The RET-mutant MTC patient (RET L629P, D631_R635DELINSG, V637R MTC) was treated with 60 mg once daily and then received successive dose escalation up to 300 mg once daily.
Figure 4B:
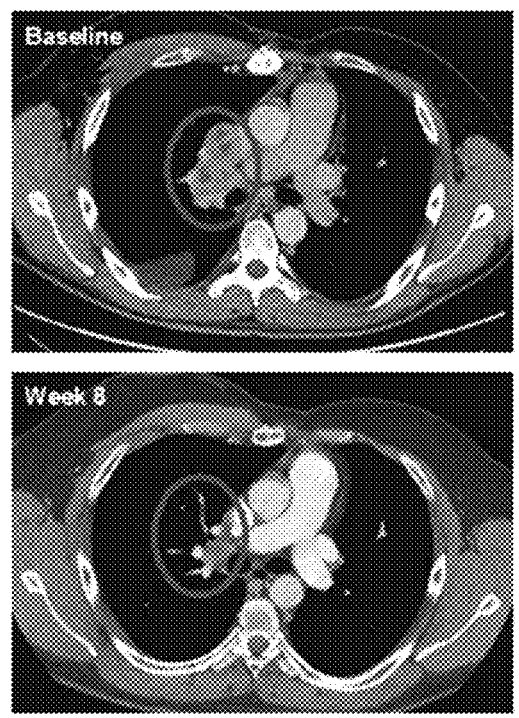
FIG. 4B is a CT scan of the same RET-mutant MTC patient of FIG. 4A at baseline (top) and after 8 weeks of Compound 1 treatment (bottom) demonstrating rapid reduction in tumor growth.

Patient 1 was a 27-year-old patient with sporadic MTC harboring multiple RET mutations (L629P, D631_R635DELINSG, and V637R). The patient was tyrosine kinase inhibitor naïve prior to the start of Compound 1 treatment with highly invasive disease that required emergent tracheostomy and extensive surgery, including total thyroidectomy, central neck dissection, bilateral levels 1 through 4 neck dissection, total thymectomy, and median sternotomy. The postoperative course was complicated by chylothorax. Multidisciplinary medical consensus was against radiotherapy to the neck, and restaging scans showed left paratracheal disease with tracheal and esophageal invasion as well as metastatic disease to the lungs and liver. The two FDA approved multi-kinase drugs for MTC (vandetanib and cabozantinib) were not considered appropriate for this patient given the associated risk of VEGFR-related toxicities that can include impaired wound healing, and increase the risk of fistula formation and hemorrhage (CAPRELSA (vandetanib) [package insert]. Cambridge, Mass.: Sanofi Genzyme; 2016; COMETRIQ (cabozantinib) [package insert]. South San Francisco, CA: Exelixix, Inc.; 2018). Therefore, the patient was enrolled on the Compound 1 clinical trial and began treatment at the second dose level (60 mg, QD). Remarkably, after 28 days of Compound 1 therapy, there was a>90% reduction in the serum tumor marker calcitonin (FIG. 4A). After 8 weeks, target lesions were reduced by 19%. After successive dose escalations of Compound 1 to 200 mg QD, the patient achieved partial response with >30% tumor reduction per Response Evaluation Criteria in Solid Tumors (RECIST) version 1.1 (FIG. 4B). This patient subsequently escalated to 300 mg QD Compound 1 and achieved a confirmed partial response (47% maximal reduction) at 10 months. Overall, carcinoembryonic antigen (CEA) levels decreased by 57% over this period. Improved health status with Compound 1 treatment allowed for removal of the patient's tracheostomy tube and a return to baseline body weight after several kilograms of weight loss prior to treatment. Compound 1 has been well tolerated throughout 11 months of continuous treatment with the only drug-related adverse event being transient grade 1 decrease in white blood cells, which resolved without drug interruption or dose modification. As of Apr. 13, 2018, the patient remains on therapy.

Figure 4C:
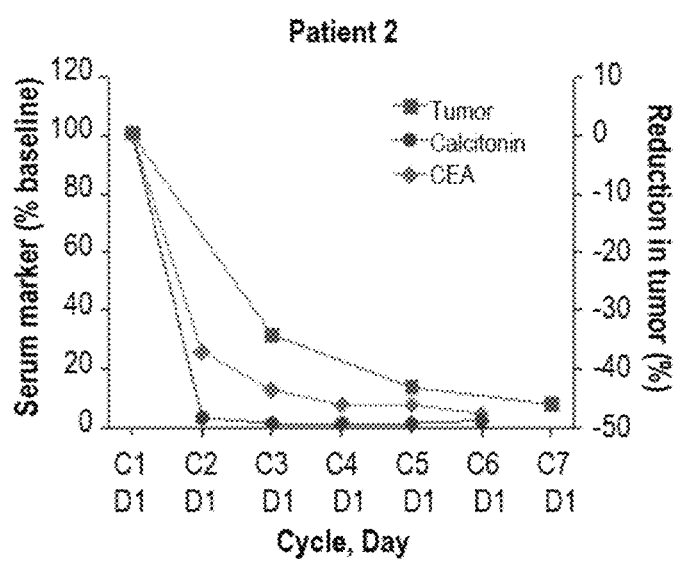
FIG. 4C is a graph which shows tumor size and the levels of calcitonin and CEA decrease in a patient with RET M918T-mutant MTC over the course of treatment with Compound 1 with 300 mg once daily.
Figure 4D:
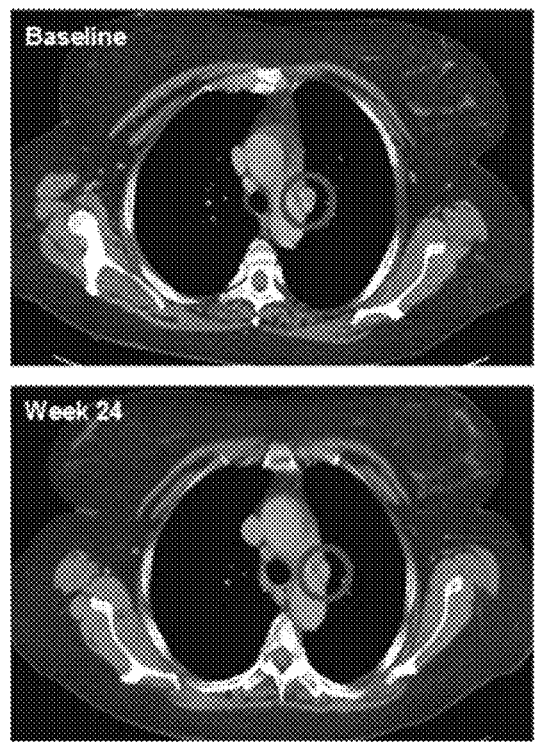
FIG. 4D is a CT scan of the RET M918T-mutant patient of FIG. 4C's tumor at baseline (top) and after 24 weeks of Compound 1 treatment (bottom).
Figure 4E:
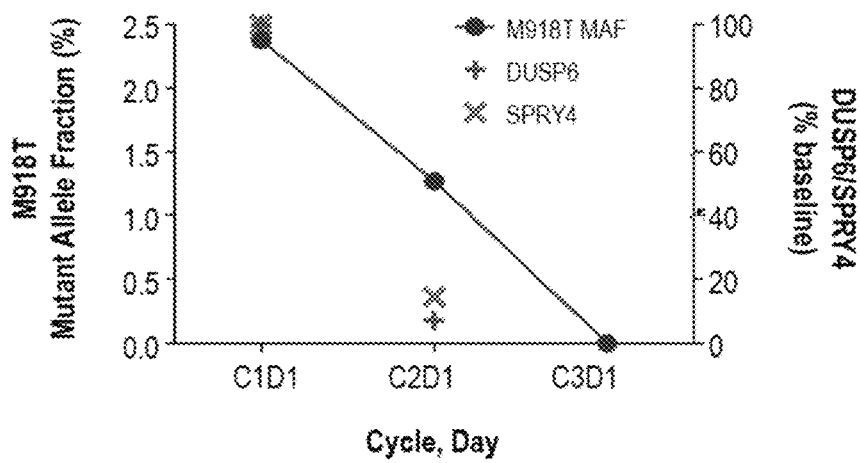
FIG. 4E is a graph which shows ctDNA analysis of RET M918T levels in plasma from an MTC patient during treatment. Pre- and post-treatment tumor biopsy revealed a 93% decrease in DUSP6 and 86% decrease in SPRY4 mRNA expression after 28 days of treatment with Compound 1.

Patient 2 was a 56-year-old with sporadic RET M918T-mutant MTC, who had responded and then progressed on vandetanib, initiated therapy with Compound 1, 300 mg QD. Early signals of clinical activity emerged within the first few weeks of Compound 1 treatment: serum calcitonin decreased>90% and CEA decreased by 75% after 28 days (FIG. 4C). RET M918T circulating tumor DNA (ctDNA) decreased by 47% after 28 days and was not detectable after 56 days. Paired tumor biopsies collected pretreatment and 28 days post-treatment demonstrated a 93% reduction in DUSP6 and an 86% reduction in SPRY4 mRNA expression, confirming RET-pathway inhibition within the tumor (FIG. 4E). Importantly, these indications of activity were confirmed by radiographic response (−35%) per RECIST 1.1 after 8 weeks (FIG. 4D). The patient tolerated Compound 1 treatment well without dose interruption; drug-related adverse events were grade 1 nausea and hyperphosphatemia. The patient continues on therapy at 8 months with a confirmed partial response (maximum 47% reduction) as of Apr. 13, 2018.

Figure 5A:
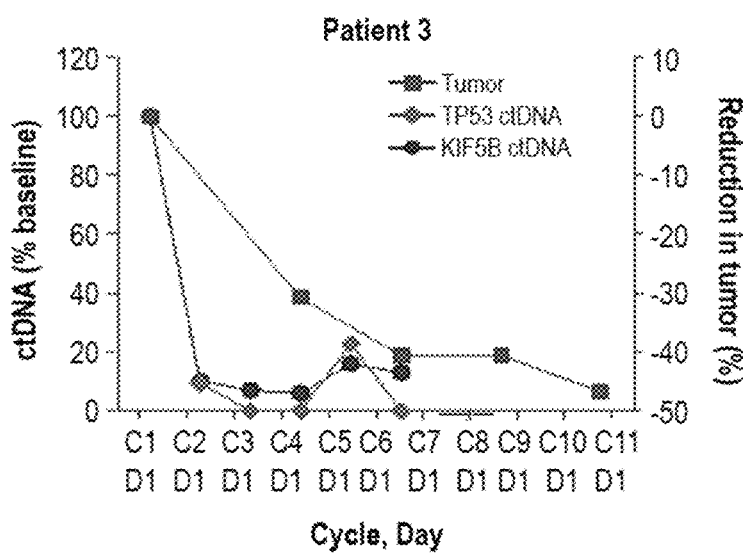
FIG. 5A is a graph which shows lung tumor and KIF5B-RET and TP53 ctDNA reduction over the course of treatment with 200 mg once daily Compound 1.
Figure 5B:
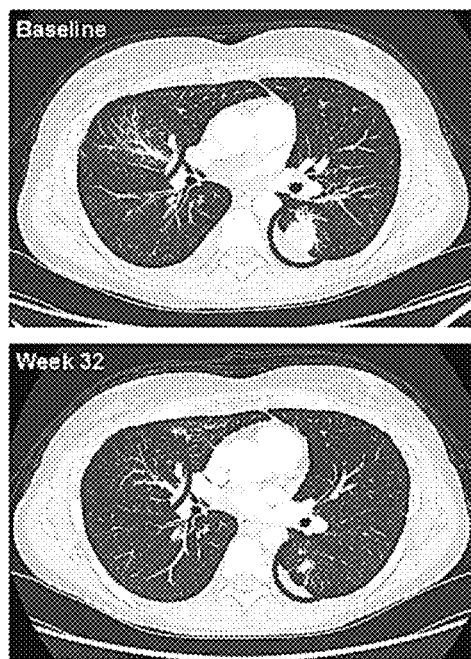
FIG. 5B is a CT scan which illustrates tumor at baseline (top) and after 32 weeks of Compound 1 treatment (bottom).

Patient 3 was a 37-year-old patient with metastatic RET-altered NSCLC, who had progressed on cisplatin, pemetrexed, and bevacizumab, had tumor tissue test positive for a RET fusion via FISH analysis. The patient initiated treatment with 200 mg QD Compound 1, and ctDNA analysis at baseline revealed a canonical KIF5B-RET fusion and co-occurring TP53 mutation. Tumor reduction (−25%) was noted at first radiographic assessment after 8 weeks of treatment and correlated with a concomitant decline in KIF5B-RET and TP53 ctDNA levels (FIG. 5A). The patient achieved a partial response on the second radiographic assessment after 16 weeks (FIG. 5B) and continues on treatment through 10 months with a confirmed partial response as of Apr. 13, 2018. As observed with the MTC patients described above, Compound 1 has been well tolerated, with all drug-related adverse events being grade 1 and including constipation (resolved), dry skin, rash, and leukopenia.

Figure 9A:
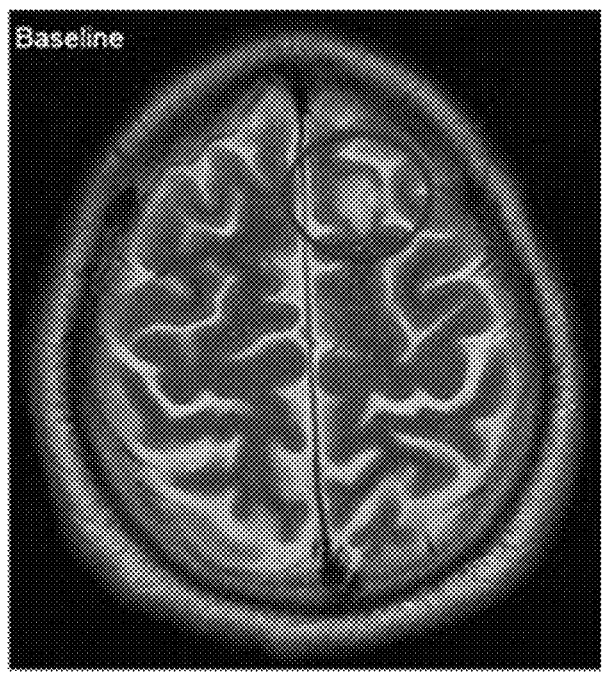
FIG. 9A is a brain CT scan at baseline prior to treatment with Compound 1.
Figure 9B:
FIG. 9B is a brain CT scan after 8 weeks of treatment with Compound 1 treatment.
Figure 10:
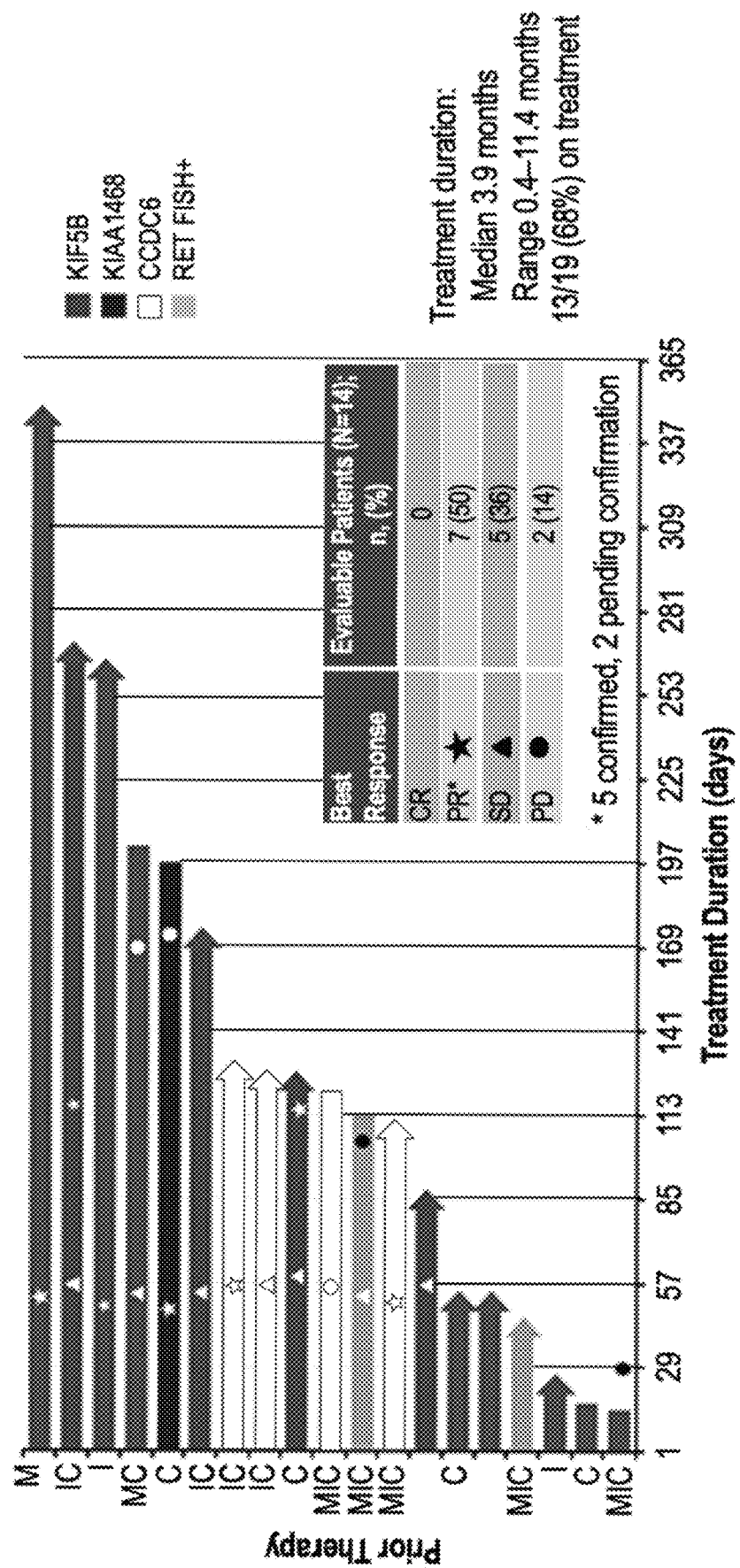
FIG. 10 is a chart which shows patient response rate in RET-altered NSCLC. Data cut-off: Apr. 6, 2018.
Figure 11A:
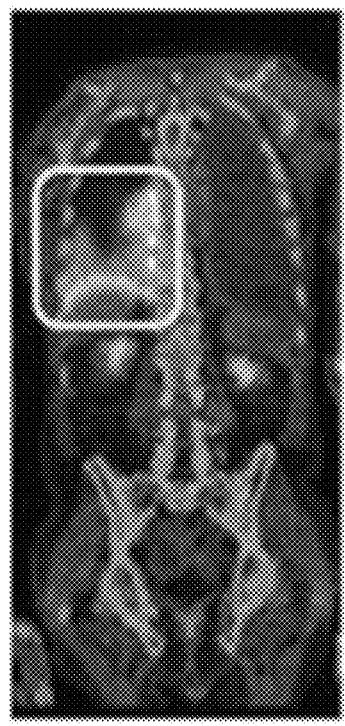
FIG. 11A is a CT scan at baseline prior to treatment with Compound 1.
Figure 11B:
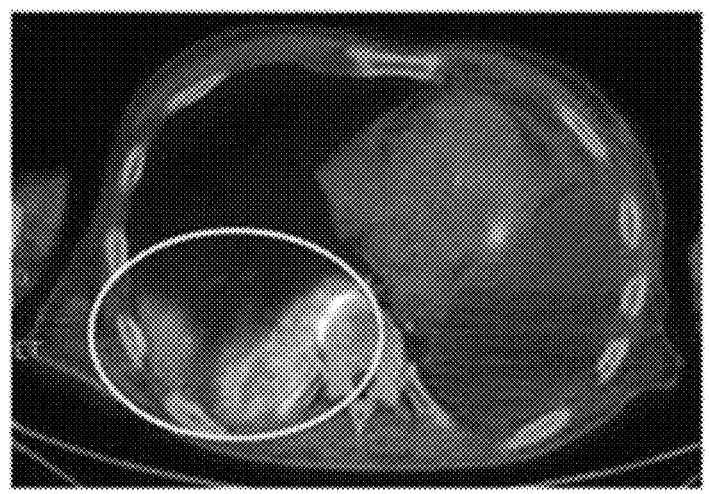
FIG. 11B is a CT scan after 8 weeks of treatment with Compound 1.
Figure 11C:
FIG. 11C is a CT scan at baseline prior to treatment with Compound 1.
Figure 11D:
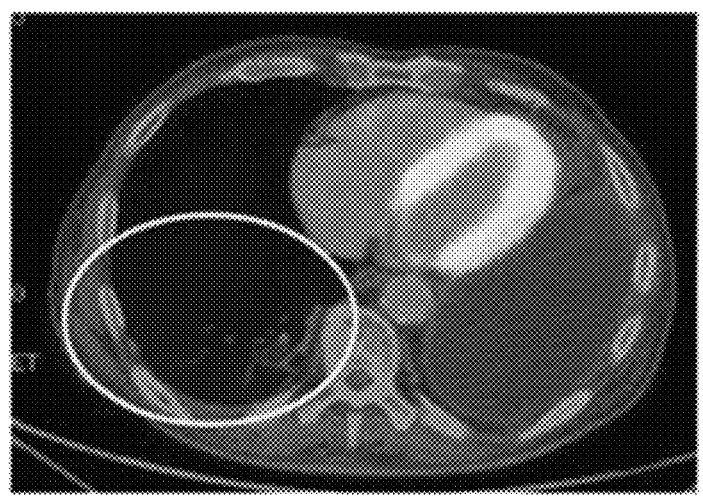
FIG. 11D is a CT scan after 8 weeks of treatment with Compound 1.
Figure 12:
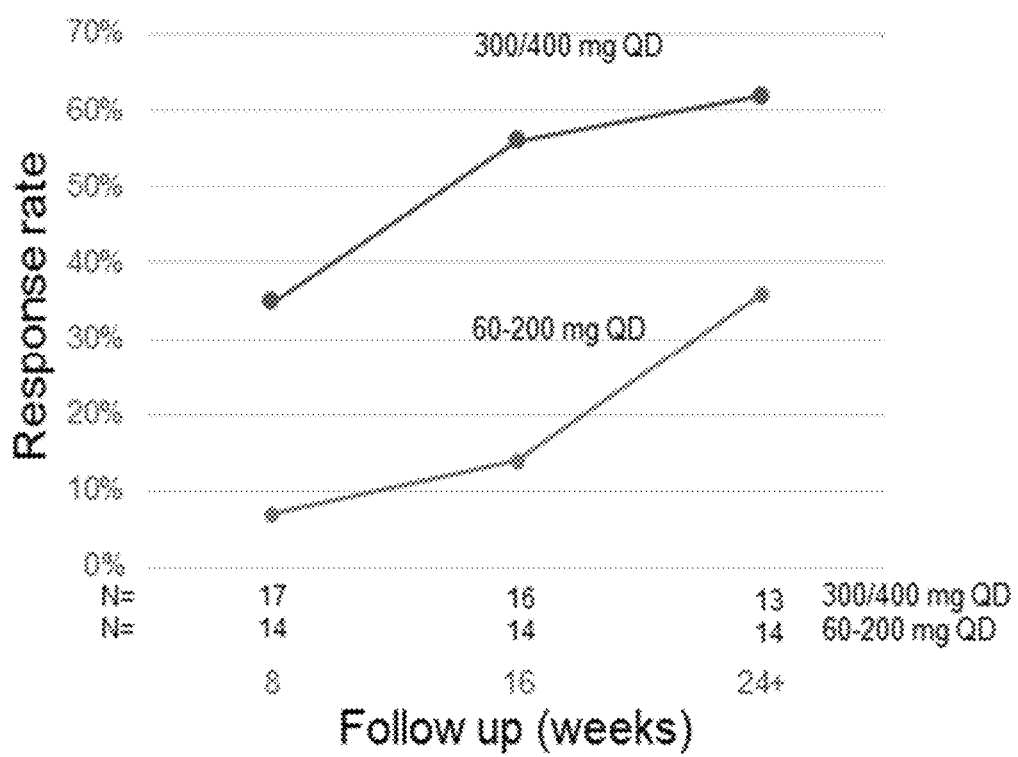
FIG. 12 is a graph which shows that the response rate in medullary thyroid cancer patients increases with dose and duration of therapy. Specifically, the graph shows the response rate for dosing Compound 1 at 60 to 200 mg once daily and 300/400 mg once daily over a period of 8 to 24+weeks.

Patient 4 was a 69-year-old patient with NSCLC, who had prior lung resection nephrectomy, and pleural drainage. The patient initiated treatment with 400 mg QD Compound 1. Tumor reduction was noted against KIF5B-RET NSCLC brain metastases (FIG. 9). Specifically, evidence of intracranial anti-tumor activity was observed in the patient. At baseline, the patient had an approximately 6 mm metastatic lesion in the brain, which appeared to resolve after 8 weeks on treatment. At the time of the 8-week assessment, the patient was determined to have stable disease.

Patient 5 was a 74-year-old former smoker with locally advanced KIF5B-RET NSCLC. The patient's CT scans are shown in FIGS. 11A-11D. The patient had received concurrent chemoradiation with cisplatin and pemetrexed, was then treated with carboplatin and nab-paclitaxel and eventually progressed. Next generation sequencing of the tumor tissue, along with FISH, revealed a KIF5B-RET fusion, and the patient was enrolled on a clinical trial testing a combination regimen of vandetanib and everolimus (NCT01582191). The patient achieved a partial response, but restaging scans performed after 11 cycles showed progressive disease, which was associated with clinical symptoms of increasing dyspnea and worsening performance status. The patient was then enrolled on the phase 1 trial of Compound 1. After 16 weeks of treatment with Compound 1 (300 mg QD), the patient had a partial response with 34% reduction of tumor volume (FIGS. 11C and 11D) and improvement of dyspnea and performance status. Compound 1 has been well tolerated throughout treatment, and the patient has not experienced drug-related adverse events as of Apr. 13, 2018.

Figure 13:
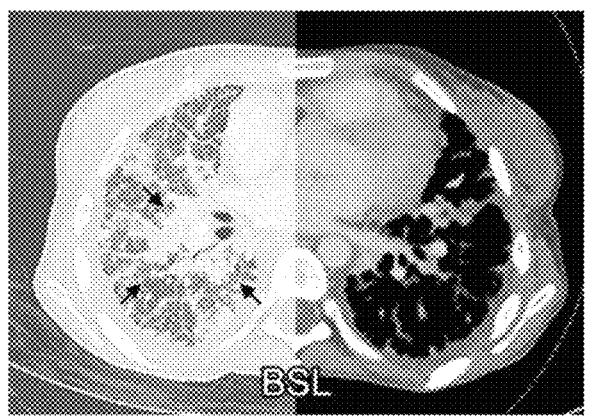
FIG. 13 is a CT scan at baseline (BSL) and after 5 months of treatment with Compound 1 at 400 mg once daily.
Figure 13:
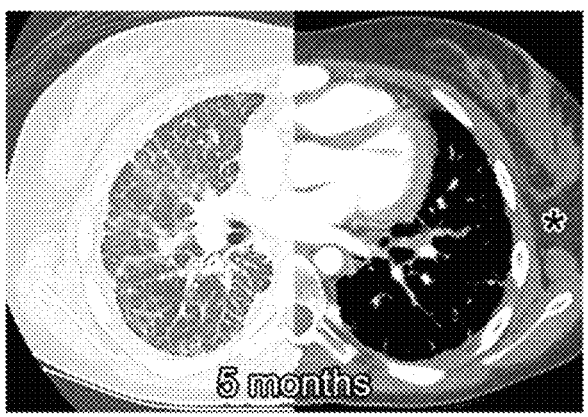

Patient 6 was a 23-year old woman with PTC, sclerosing variant (CCDC$_6$-RET fusion), who presented 6 years ago with symptomatic diffuse lung metastases requiring supplemental oxygen, since diagnosis. She had progressed on sorafenib and lenvatinib. She initiated treatment with Compound 1 at 400 mg once daily. FIG. 13 shows tumor reduction after 5 months of treatment with Compound 1. Within 5 months, she was weaned to room air.

Measuring ctDNA Levels

Levels of one example effect marker, ctDNA in plasma (e.g., KIF5B or TP53 ctDNA), may be assessed using the PlasmaSELECT™-R64 NGS panel (Personal Genome Diagnostics, Baltimore, Md.). PlasmaSELECT™ 64 analyzes circulating tumor DNA for genetic alterations in cancer. Specifically, PlasmaSELECT™ 64 evaluates a targeted panel of 64 well-characterized cancer genes. Cell-free DNA is extracted from plasma and prepared using proprietary methods that accommodate low abundance sample DNA. Samples are then processed using a proprietary capture process and high coverage next-generation sequencing.

Steady State Plasma Concentration, RET IC$_{90}$ and Brain IC$_{90}$ (Predicted)

Figure 6A:
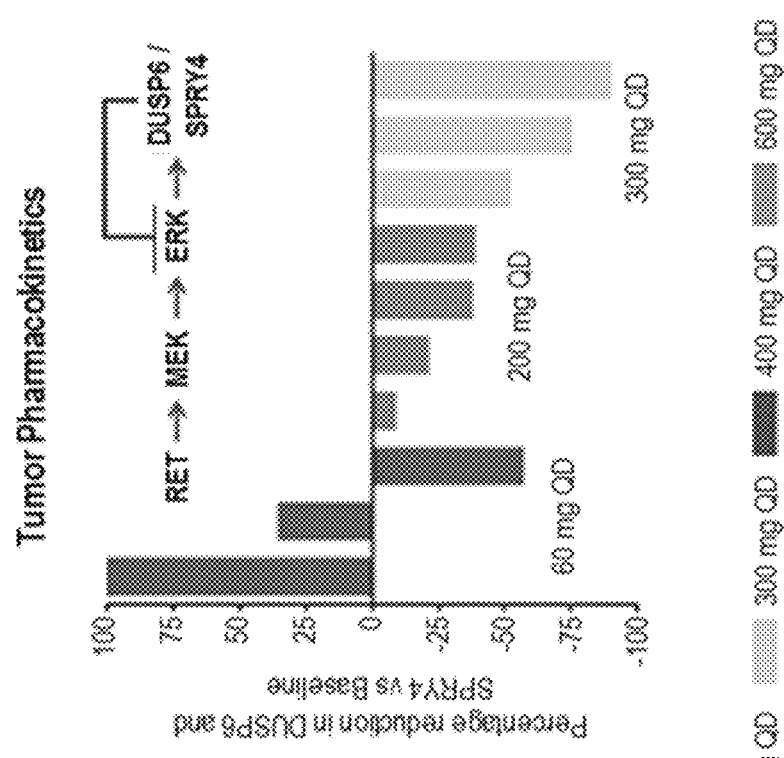
FIG. 6A is a graph which shows the mean plasma concentration (ng/mL) vs. time (h)
Figure 6B:
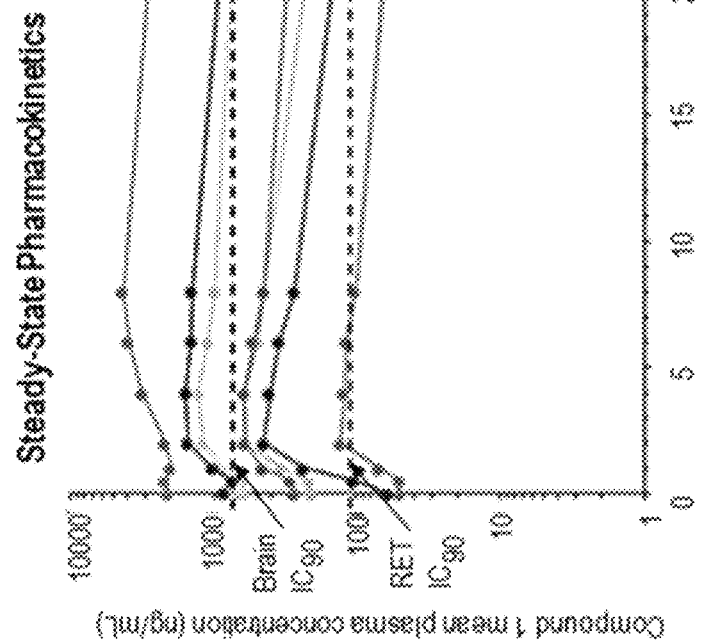
FIG. 6B is a bar graph which shows the percent change from baseline in mean gene expression levels of DUSP6 and SPRY4.
Figure 7A:
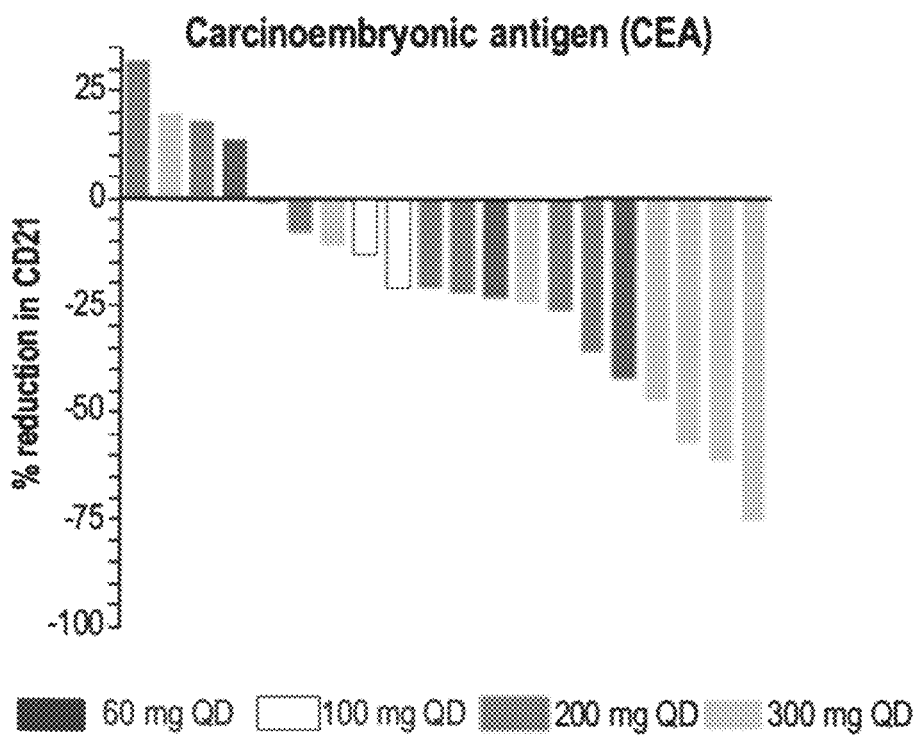
FIG. 7A is a bar graph which shows dose-dependent reduction in CEA in patients measured on cycle 2, day 1.
Figure 7B:
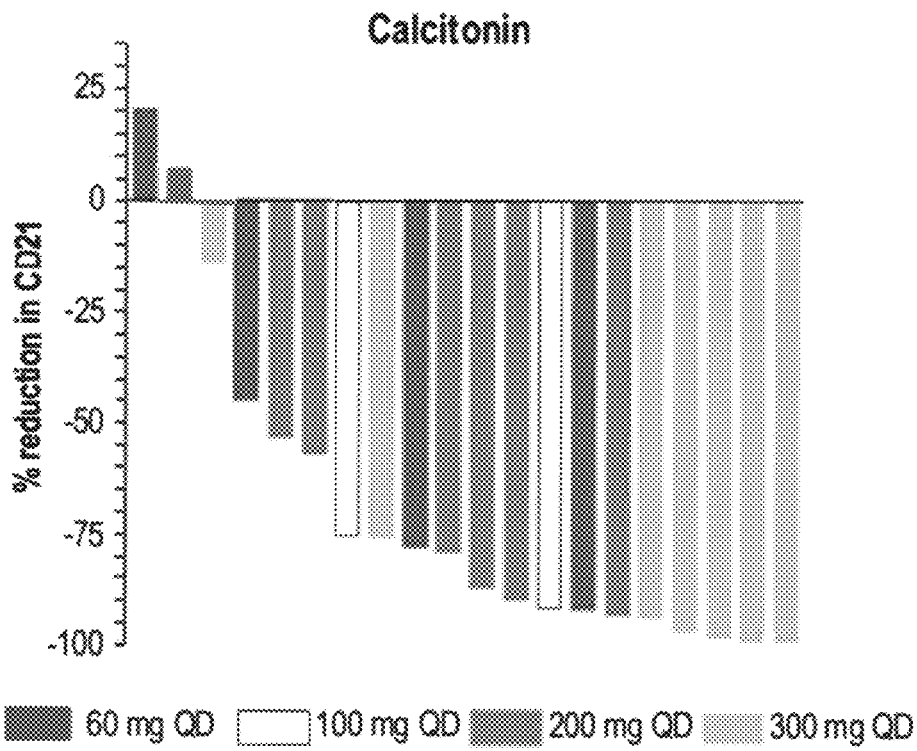
FIG. 7B is a bar graph which shows dose-dependent reduction in calcitonin in patients measured on cycle 2 day 1.
Figure 8:
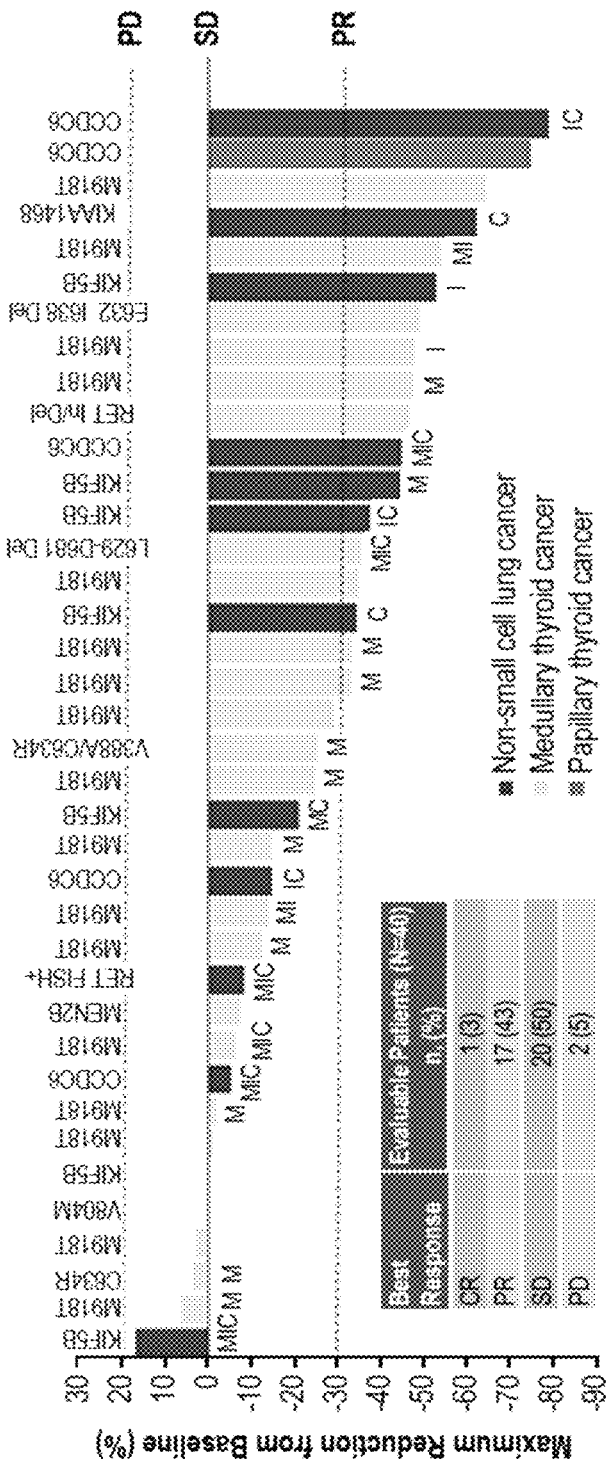
FIG. 8 is a waterfall plot which shows maximum tumor reduction-sum of diameter change from baseline percent—from patients in the phase I clinical study. Data cut-off: Apr. 6, 2018.

Blood samples were collected at pre-determined time points from patients dosed with 30 to 600 mg Compound 1 orally once daily. Plasma samples were analyzed for Compound 1 using a validated liquid chromatography-tandem mass spectrometry (LC-MS/MS) method. The plasma Compound 1 concentration-time data were graphed using Phoenix WinNonlin© (Version 6.4, Certara L. P.) or Graphpad Prism (Version 7.02). FIG. 6A shows the plasma concentration-time profile of Compound 1 at steady state. The RET IC$_{90}$ and brain IC$_{90}$ (predicted) are based on projections and extrapolations based on PK and PD data in animals.

A twice a day (BID) dosing schedule was also explored as part of the phase I clinical trial. The BID dosing schedule started at a 300 mg total daily dose (200 mg in the morning, 100 mg in the evening). A total of 9 patients were enrolled into the BID dose escalation: 4 patients at 300 mg total daily dose (200 mg in the morning, 100 mg in the evening) and 5 patients at 200 mg total daily dose (100 mg BID). Of the first 4 patients enrolled at the 300 mg total daily dose, 2 patients experienced dose limiting toxicities (DLTs) of Grade 3 hypertension and the dose was subsequently de-escalated to 100 mg BID. Two of 5 patients at 100 mg BID experienced DLTs, including 1 patient with Grade 3 hypertension and 1 patient with Grade 3 tumor lysis syndrome. Based on overall safety, exposure, and tolerability, QD was the superior dosing schedule and chosen for the dose expansion.

All publications and patents mentioned herein are hereby incorporated by reference in their entirety.

The invention claimed is:

1. A method of treating a subject with a rearranged during transfection (RET)-altered non-small cell lung cancer (NSCLC), the method comprising orally administering to the subject once daily 200 mg, 300 mg, or 400 mg of Compound 1 or a pharmaceutically acceptable salt thereof, wherein Compound 1 is:

(Compound 1)

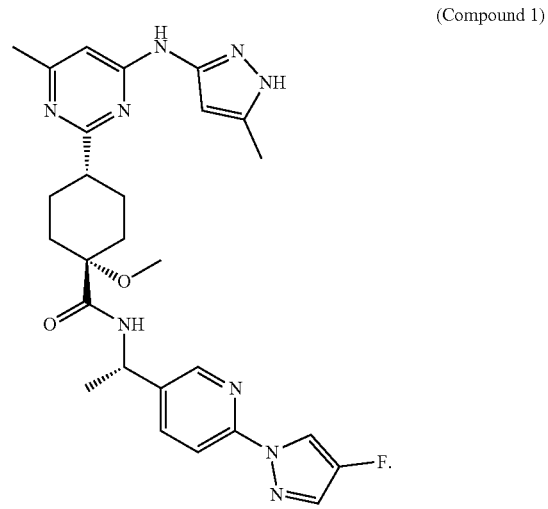 [SMILES: CO[C@]1(C(=O)N[C@@H](C)c2ccc(-n3cc(F)cn3)nc2)CC[C@H](c2nc(C)cc(Nc3cc(C)[nH]n3)n2)CC1]

2. The method of claim 1, wherein the NSCLC has a RET-gene rearrangement.

3. The method of claim 2, wherein the RET-gene rearrangement is a RET fusion.

4. The method of claim 3, wherein the RET fusion is selected from CLIP1, PIBF1, BCR, FGFRIOP, CEP55, CUX1, MYH13, PTClex9, MPRIP, CCDC6, KIF5B, TRIM33, MBD1, RAB61P2, PRKAR1A, TRIM24, KTN1, HOOK3, TRIM27, AKAP13, FKBP15, ERC1, KIAA1468, KIAA1217, NCOA4, GOLGA5, SPECC1L, TBL1XR1 and ACBD5.

5. The method of claim 3, wherein the RET fusion is selected from CCDC6, KIF5B, TRIM33, TRIM24, and NCOA4.

6. The method of claim 3, wherein the RET fusion is KIF5B.

7. The method of claim 3, wherein the RET fusion is CCDC6.

8. The method of claim 1, wherein the NSCLC is metastatic NSCLC.

9. The method of claim 1, wherein the subject was previously treated with platinum.

10. The method of claim 9, wherein the platinum is selected from cisplatin and carboplatin.

11. The method of claim 1, wherein the subject was previously treated with cabozantinib or vandetanib or both.

12. The method of claim 8, wherein the subject is orally administered 300 mg of Compound 1 once daily.

13. The method of claim 8, wherein the subject is orally administered 400 mg of Compound 1 once daily.

14. The method of claim 1, wherein the subject is orally administered 200 mg of Compound 1 once daily.

15. The method of claim 1, wherein the Compound 1 or a pharmaceutically acceptable salt thereof is administered as one or more solid dosage forms.

16. The method of claim 15, wherein the one or more solid dosage forms are tablets.

17. The method of claim 15, wherein the one or more solid dosage forms are capsules.

18. A method of treating a subject with a metastatic rearranged during transfection (RET)-altered non-small cell lung cancer (NSCLC) comprising a RET fusion, the method comprising orally administering to the subject once daily 300 mg of Compound 1 or a pharmaceutically acceptable salt thereof, wherein Compound 1 is:

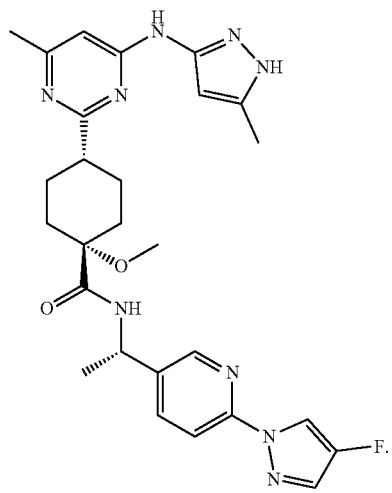

(Compound 1)

19. A method of treating a subject with a metastatic rearranged during transfection (RET)-altered non-small cell lung cancer (NSCLC) comprising a RET fusion, the method comprising orally administering to the subject once daily 400 mg of Compound 1 or a pharmaceutically acceptable salt thereof, wherein Compound 1 is:

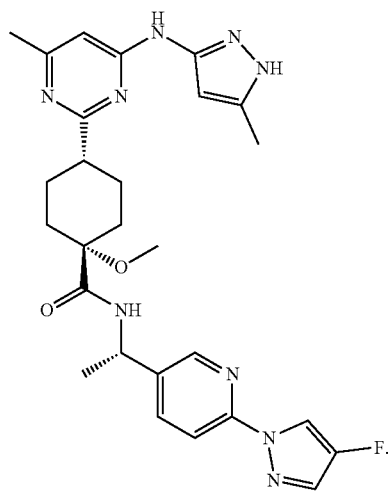

(Compound 1)

* * * * *